US007267823B2

(12) United States Patent
Hart et al.

(10) Patent No.: US 7,267,823 B2
(45) Date of Patent: Sep. 11, 2007

(54) *EBOLA* PEPTIDES AND IMMUNOGENIC COMPOSITIONS CONTAINING SAME

(75) Inventors: Mary Katherine Hart, Frederick, MD (US); Julie Ann Wilson, Birmingham, AL (US); Gene Garrard Olinger, Jr., Frederick, MD (US); Michael Adam Bailey, Frederick, MD (US)

(73) Assignee: United States of America as Represented by the Secretary of the Army, Washington, DC (US)

( * ) Notice: Subject to any disclaimer, the term of this patent is extended or adjusted under 35 U.S.C. 154(b) by 379 days.

(21) Appl. No.: 10/384,976

(22) Filed: Mar. 10, 2003

(65) Prior Publication Data
US 2003/0224015 A1 Dec. 4, 2003

Related U.S. Application Data

(63) Continuation-in-part of application No. 09/337,946, filed on Jun. 22, 1999, now abandoned.

(60) Provisional application No. 60/091,403, filed on Jun. 29, 1998.

(51) Int. Cl.
*A61K 39/12* (2006.01)
*A61K 38/00* (2006.01)

(52) U.S. Cl. .............................. 424/204.1; 424/185.1; 424/186.1; 530/300; 530/325; 530/326

(58) Field of Classification Search ............. 424/185.1, 424/186.1, 204.1; 530/300, 325, 326
See application file for complete search history.

(56) References Cited

U.S. PATENT DOCUMENTS

| 5,792,462 | A | 8/1998 | Johnston et al. ......... 424/199.1 |
| 5,977,316 | A | 11/1999 | Chatterjee et al. ....... 530/387.2 |
| 6,340,463 | B1 | 1/2002 | Mitchell et al. ......... 424/263.1 |
| 6,630,144 | B1 | 10/2003 | Hart et al. ................... 424/159 |
| 6,713,069 | B1 * | 3/2004 | Gallaher .................. 424/218.1 |
| 2002/0164582 | A1 | 11/2002 | Hart et al. | |
| 2004/0053865 | A1 | 3/2004 | Hart et al. | |
| 2004/0146859 | A1 | 7/2004 | Hart et al. | |

FOREIGN PATENT DOCUMENTS

| WO | WO96/37616 | 11/1996 |
| WO | WO99/32147 | 7/1999 |
| WO | WO 00/00616 | 1/2000 |
| WO | WO 00/00617 | 1/2000 |
| WO | WO 01/016183 | 3/2001 |

OTHER PUBLICATIONS

Hart, Mary Kate, Vaccine reserach efforts for filoviruses, International Journal for Parasitology, 2003, 33:583-595.*

Voichkov et al., "The envelope glycoprotein of Ebola virus contains an immunosuppressive-like domain similar to oncogenic retroviruses", FEBS Letters, vol. 305, No. 3, pp. 181-184 (Jul. 1992).

Sanchez et al., "Biochemical Analysis of the Secreted and Virion Glycoproteins of Ebola Virus", J. Virology, Aug. 1998, vol. 72, pp. 6442-6447.

Wilson et al., "Epitopes Involved in Antibody-Mediated Protection from Ebola Virus", Science, vol. 387, Mar. 3, 2000, pp. 1664-1666.

Ichihashi and Oie, "Neutralizing Epitope on Penetration Protein of Vaccinia Virus", Virology 220, pp. 491-494 (1996).

Wolffe et al., "A myristylated membrane protein encoded by the vaccinia virus L1R open reading frame is the target of potent neutralizing monoclonal antibodies", Virology 211, pp. 53-63 (1995).

Roper et al., "Extracellular vaccinia virus envelope glycoprotein encoded by the A33R gene", J. Virology, Jun. 1996, vol. 70, No. 6, pp. 3753-3762.

Isaacs et al., "Characterization of a vaccinia virus-encoded 42-kilodalton class 1 membrane glycoprotein component of the extracellular virus envelope", J. Virology, Dec. 1992, vol. 66, No. 12, pp. 7217-7224.

Abstract W33-5, "DNA vaccination against poxviruses using combinations of IMV and EEV immungens", presented Jul. 2000, American Society for Virology Meeting, p. 113.

Abstract P23-6, "DNA immunization with the vaccinia L1R and/or A33R genes", Jul. 1998, poster at American Society for Virology meeting.

Meyer et al., "Identification of binding sites for neutralizing monoclonal antibodies on the 14-kDa fusion protein of orthodox viruses", Virology 200, Short Communications, pp. 778-783 (1994).

Czerny and Mahnel, "Structural and functional analysis of orthopoxvirus epitope with neuralizing monoclonal antibodies", J. General Virology (1990) vol. 71, pp. 2341-2352.

Hooper et al., "DNA vaccination with vaccinia virus L1R and A33R genes protects mice against a lethal poxvirus challenge", Virology 266, pp. 329-339 (2000).

Vazquez and Esteban, "Identification of functional domains in the 14-kilodalton envelope protein (A27L) of vaccinia virus", J. Virology, Nov. 1999, vol. 73, No. 11, pp. 9098-9109.

Vazquez et al., "The vaccinia virus 14-kilodalton (A27L) fusion protein forms a triple coiled-coil structure and interacts with the 21-kilodalton (A17L) virus membrane protein through a C-terminal of alpha-helix", J. Virology, Dec. 1998, vol. 72, No. 12, pp. 10126-10137.

Rodriguez et al., "The vaccinia virus 14-kilodalton fusion proteins forms a stable complex with the processed protein encoded by the vaccinia virus A17L gene", J. Virology, Jun. 1993, vol. 67, No. 6, pp. 3435-3440.

(Continued)

*Primary Examiner*—Stacy B. Chen
(74) *Attorney, Agent, or Firm*—Elizabeth Arwine

(57) ABSTRACT

Using CTL epitopes to the *Ebola* GP, NP, VP24, VP30, VP35 and VP40 virion proteins, a method and composition for use in inducing an immune response which is protective against infection with *Ebola* virus is described.

6 Claims, 6 Drawing Sheets

OTHER PUBLICATIONS

Lai et al., "The purified 14-kilodalton envelope protein of vaccinia virus produced on *Escherichia coli* induces virus immunity in animals", J. Virology, Oct. 1991, vol. 65, No. 10, pp. 5631-5635.

Rodriguez and Esteban, "Mapping and nucleotide sequence of the vaccinia virus gene that encodes a 14-kilodalton fusion protein", J. Virology, Nov. 1987, vol. 61, No. 11, pp. 3550-3554.

Rodriguez et al., "Isolation and characterization of neutralizing monoclonal antibodies to vaccinia virus", J. Virology, Nov. 1985, vol. 56, No. 2, pp. 482-488.

NCBI PubMed medline, Abstract for Rodriguez et al., "Isolation and characterization of neutralizing monoclonal antibodies to vaccinia virus", J. Virology, Nov. 1985, vol. 56, No. 2, pp. 482-488.

Lin et al., "Vaccinia virus envelope H3L protein binds to cell surface heparan sulfate and is important for intracellular mature virion morphorogenesis and a virus infection in vtiro and in vivo", J. Virology, Apr. 2000, vol. 74, No. 7, pp. 3353-3365.

Gordon et al., "A prominent antigenic surface polypeptide involved in the biogenesis and function of the vaccinia virus envelope", Virology 181, pp. 671-686 (1991).

Ichihashi et al., "Identification of a vaccinia virus penetration protein", Virology 202, pp. 834-843 (1994).

Demkowicz et al., "Identification and characterization of vaccinia virus genes encoding proteins that are highly antigenic in animals and are immunodominant in vaccinated humans", J. Virology, jan. 1992, vol. 66, No. 1, pp. 386-398.

Wilson et al., "Ebola virus: the search for vaccines and treatments", CMLS Cell., Mol Life Sci., 58 (2001) pp. 1-16.

Pushko et al, "Venezuelan Equine Encephalitis virus replicon vector: immunogenicity studies with ebola NP and GP genes in guinea pigs", Vaccines 97, Molecular Approaches to the Control of Infectious Diseases, Cold Spring Harbor Laboratory Press, 1997, pp. 253-258.

Geisbert et al., "Evaluation in nonhuman primates of vaccines against Ebola virus", Perspectives, Emerging Infectious Diseases, vol. 8, No. 5, May 2002, pp. 503-507.

Pushko et al., "Recombinant RNA replicons derived from attenuated Venezuelan equine encephalitis virus protect guinea pigs and mice from Ebola hemorrhagic fever virus", Vaccine 11 (2000) pp. 1-12.

Wilson et al., "Vaccine potential of Ebola virus VP24, VP30, VP35, and VP40 proteins", Virology 286, pp. 384-390 (2001).

Wilson and Hart, "Protection from Ebola virus mediated by cytotoxic T lymphocytes specific for the viral nucleoprotein", J. Virology, Mar. 2001, vol. 75, No. 6, pp. 2660-2664.

Maruyama et al., "Recombinant human monoclonal antibodies to Ebola virus", J. Infectious Diseases, 1999, 179 (Suppl 1), pp. S235-S239.

Jahrling et al., "Evaluation of immune globulin and recombinant interferon-alpha2b for treatment of experimental Ebola virus infections", J. Infectious Diseases, 1999, 170 (Suppl 1), pp. S224-S234.

Volchkov et al., "Release of viral glycoproteins during Ebola virus infection", Virology 245, pp. 110-119 (1998).

GenBank, Database printout, for Sanchez et al., Ebola virus nuceoprotein, polymerase copmlex protein (VP35), matrix protein (VP40), glycoprotein (GP), minor nucleoprotein (VP30), and membrance-associates structural protein (VP24), Oct. 14, 1997 (7 pages).

Hevey et al., "Antigenicity and vaccine potential of Marburg virus glycoprotein expressed by baculovirus recombinants", Virology 239, pp. 206-216 (1997).

Maruyama et al., "Ebola virus can be effectively neutralized by antibody produced in natural human infection", J. Virology, Jul. 1999, vol. 73, No. 7, pp. 6024-6030.

Wilson et al., "Ebola virus: the search for vaccines and treatments", CMLS Cell. Mol. Life Sci. 58 (2001), pp. 1826-1841.

Maruyama et al., "Recombinant human monoclonal antibodies to Ebola virus", J. Infectious Diseases, 1999, 179 (Suppl 1), pp. S235-S239.

Sanchez et al., "The virion glycoproteins of Ebola viruses are encoded in two reading frames and are expressed through transcriptional editing", PNAS, USA, vol. 93, pp. 3602-3607, Apr. 1996.

Jahrling et al., "Passive immunization of Ebola virus-infected cynomolgus monkeys with immunoglobulin from hyperimmune horses", Arch Virol, 1996 (Suppl) 11, pp. 135-140.

Parren et al., "Pre-and postexposure prophylaxis of ebola virus infection in an animal model by passive tranfer of a neutraling human antibody," J. Virology, Jun. 2002, vol. 76, No. 12, pp. 6408-6412.

Wilson et al., "Epitopes involved in an antobody-mediated protection from ebola virus",Science, vol. 287, pp. 1664-1666 Mar. 3, 2000.

Sanchez et al., "Detection and molecular characterization of ebola viruses causing disease in human and nonhuman primates", J. Infectious Diseases, 1999, vol. 179 (Suppl. 1), pp. S164-S169.

Sanchez et al., "Biochemical analysis of the secreted and virion glycoproteins of ebola virus", J. Virology, Aug. 1998, vol. 72, No. 8, pp. 6442-6447.

Khaw et al., "Technetium-99m labeling of antibodies to cardiac myosin fab and to human fibrinogen", Radiochemistry and Radiopharmaceuticals, J. Nucl. Med., vol. 23, No. 11, pp 1011-1019, Nov. 1982.

Farid et al., "Idiotypes, paratopes and molecular mimicry", pp 1-5, and "An idiotype approach for a vaccine against hepatitus B surface antigen", pp. 285-300, both in Anti-Idiotypes, Receptors, and Molecular Mimicry, Ivy Springer-Verlag, 1988.

Kabat et al., Sequence of proteins of immunological interest, vol. 1, Fifth ed., pp. xiv-xix and 33 pages of sequences (1991).

Waldmann, "Manipulation of T-cell responses with monoclonal antibodies", Ann. Rev. Immunol. (1989) 7:407-444.

Kennedy et al., "Review: Protein-protein coupling reactions and the applications of protein conjugates", Clinica Chimica Acts 70 (1976) pp. 1-31.

"Continuous cultures of fused cells secreting antibody of predefinied specificity", Nature, vol. 256, pp. 495-497 (1975).

Volchkov et al., "Processing of the ebola virus glycoprotein by the proprotein convertase furin", PNAS USA, vol. 95, pp. 5762-5767 (May 1998).

Stiles et al., "Production and characterization of monoclonal antibodies against NAJA NAJA ATRA cobrotoxin ", Toxicon, vol. 29, No. 10, pp. 1195-1204 (1991).

Feldmann et al., "Marburg virus, a filovirus: messenger RNAs, gene order, and regulatory elements of the replication cycle", Virus Research, 24 (1992) pp. 1-19.

Peters and LeDuc, "An introduction to ebola: the virus and the disease", J. Infectious Diseases, 1999, vol. 179 (Suppl 1), pp. ix-xvi.

Kudoyarova-Zubavichene et al., "Preparation and use of hyperimmune serum for prophylaxis and therapy of ebola virus infections", J. Infectious Diseases, 1999, vol. 179 (Suppl 1), pp. S218-223.

Moe et al., "Plaque assay for ebola virus", J. Clinical Microbiology, Apr. 1981, vol. 13, No. 4, pp. 791-793.

Waldmann, "Manipulation of T-cell repsonses wit hmonoclonal antibodies", Ann. Rev. Immunol., 1989, vol. 7, pp. 407-444.

Mikhailov et al., "An evaluation of the possibility of ebola fever specific prophylaxis in baboons", Voprosy Virusologii, No. 2, pp. 82-84, 1994.

Harlow and Lane, "Antibodies: A Laboratory Manual", Ch. 6, pp. 210-213 (Cold Spring Harbor Laboratory, New York) 1988.

Schuurs and Van Weeman, "Review Enzyme-Immunoassay", Clinica Chimica Acta, 81 (1977), pp. 1-40.

PubMed Abstract from National Library of Medicine, Sanderson et al., "The vaccinia virus A27L protein is needed for the microtubule-dependent transport of intracellular mature virus particles", from Virology 1999, 264(2), at pp. 298-318.

Gilligan et al., "Assessment of protective immunity conferred by recombinant vaccinia viruses to guinea pigs challenged with ebola virus", Vaccines 97, 1997, pp. 87-92.

Xu et al., "Immunization for ebola virus infection", Nature Medicine, NO.v 4, No. 1, Jan. 1998, pp. 37-42.

Davis et al., "A viral vaccine vector that expresses foreign genes in lymph nodes and protects against mucosal challenge", J. Virology, Jun. 1996, vol. 70, No. 6, pp. 3781-3787.

Grieder et al., "Specific restriction in the progression of Venezuelan equine encephalitis virus-induced disease resulting from single amino acid changes in glycoproteins", Virology 206, pp. 994-1006 (1995).

Volchkov et al., "GP mRNA of ebola virus is edited by the ebola virus polymerase and by T7 and vaccinia virus polymerases", Virology 214, pp. 421-430 (1995).

Sanchez et al., "Variation in the glycoprotein and the VP35 genes of the Marburg virus strains", Virology 240, pp. 138-146 (1998).

Vanderzanden et al., "DNA vaccines expressing either the GP or NP genes of ebola virus protect mice from lethal challenge", Virology 246, pp. 134-144 (1998).

Sanchez et al., "The nucleoprotein gene of ebola virus: cloning, sequencing, and in vitro expression", Virology 170, pp. 81-91 (1989).

Sanchez et al., "Sequence analysis of the ebola virus genome: organization, genetic elements, and comparison with the genome of Marburg virus", Virus Research, 29, pp. 215-240 (1993).

Abstract XP-002131517, Pushko et al., "Venezuelan equine encephalitis virus replicon vector: immunogenicity studies with ebola NP and GP genes in guinea pigs", 1997.

Nicolet and Paulnock, "Promoter analysis of an interferon-inducible gene associated with macrophage activation", J. Immunology, 1994, pp. 152-162.

Hart et al., "Priming of anti-human immunoeficiency virus (HIV) CD8+ cytotoxic T cells in vivo by carrier-free HIV synthetic peptides", PNAS USA, vol. 88, pp. 9448-9452 (Nov. 1991).

Elliott et al., "Ebola protein analyses for the determination of genetic organization", Arch Virol (1993), 133:423-436.

Bukreyev et al., "The VP35 and VP40 proteins of filoviruses; Homology between Marburg and Ebola viruses", FEBS, vol. 322, No. 1, pp. 41-46, (May 1993).

Hevey et al., "Marburg virus vaccines based upon alphavirus replicons protect guinea pigs and nunhuman primates", Virology 251, pp. 28-37 (1998).

Pushko et al., "Replicon-helper systems from attenuated Venezuelan equine encephalitis virus: expression of heterologous genes in vitro and immunization against heterologous pathogens in vivo," Virology 239, pp. 389-401 (1997).

Bray et al., "A mouse model for evaluation of prophylaxis and therapy of ebola hemorrhagic fever", J. Infectious Diseases, 1998, vol. 178, pp. 651-661.

Sullivan et al., "Accelerated vaccination for Ebola virus haemorrhagic fever in non-human primates", Letters to Nature, Nature, vol. 424, Aug. 7, 2003, pp. 681-684.

Sullivan et al., "Development of a preventive vaccine for Ebola virus infection in primates", Letters to Nature, Nature, 2000 (4 pages).

Sanchez et al., "Filoviridae: Marburg and Ebola Viruses", Chapter 40, Fields Virology, 4th Ed., 2001, Lippincott Williams and Wilkins, Philadelphia, editors: Knipe et al, pp. 1249-1304.

Hart, "Vaccine research efforts for filoviruses", International Journal for Parasitology, 33 (2003) 583-595.

Wilson et al., "Ebola virus: the search for vaccines and treatments", CMLS 58 (2001), 1826-1841.

Bukreyev et al., "The VP35 and VP40 proteins of filoviruses", FEBS, vol. 322, No. 1, pp. 41-46, May 1993.

Elliott et al., "Ebola protein analyses for hte determination of genetic organization", Arch. Virol. (1993), 133:423-436.

Elliott et al., "Descriptive Analysis of Ebola Virus Proteins", Virology, vol. 147, No. 1 1985, pp. 169-176.

European Search Report in corresponding European application No. 04775833.9, mailed Aug. 8, 2006, 7 pages.

Rao et al., "Cytotoxic T lymphocytes to Ebola Zaire virus are induced in mice by immunization with liposomes containing lipid A," Vaccine 17 (1999) pp. 2991-2998.

Volchkova et al., "Delta-peptide is the corboxy-terminal cleavage fragment of the nonstructural small glycoprotein sGP of Ebola virus", Virology 265, 1999, pp. 164-171.

* cited by examiner

"Normal" Alphavirus Genome

VEE Virus Replicon Containing Foreign Gene

Helper RNAs Encoding VEE Virus Structural Proteins which contain attenuating mutations Co-transfect Replicon and helper RNAs into BHK cells VEE Replicon Particle Containing Foreign Gene

FIGURE 4

Ebola Proteins Expressed from VEE Replicons

EBOLA PEPTIDES AND IMMUNOGENIC COMPOSITIONS CONTAINING SAME

BACKGROUND OF THE INVENTION

This application is a continuation-in-part of U.S. utility application Ser. No. 09/337,946, filed Jun. 22, 1999 now abandoned, which claims priority from U.S. provisional application 60/091,403 (filed Jun. 29, 1998). The entire contents of both applications are incorporated herein by reference.

Ebola viruses, members of the family Filoviridae, are associated with outbreaks of highly lethal hemorrhagic fever in humans and nonhuman primates. The natural reservoir of the virus is unknown and there currently are no available vaccines or effective therapeutic treatments for filovirus infections. The genome of Ebola virus consists of a single strand of negative sense RNA that is approximately 19 kb in length. This RNA contains seven sequentially arranged genes that produce 8 mRNAs upon infection (FIG. 1). Ebola virions, like virions of other filoviruses, contain seven proteins: a surface glycoprotein (GP), a nucleoprotein (NP), four virion structural proteins (VP40, VP35, VP30, and VP24), and an RNA-dependent RNA polymerase (L) (Feldmann et al.(1992) Virus Res. 24, 1-19; Sanchez et al.,(1993) Virus Res. 29, 215-240; reviewed in Peters et al. (1996) In Fields Virology, Third ed. pp. 1161-1176. Fields, B. N., Knipe, D. M., Howley, P. M., et al. eds. Lippincott-Raven Publishers, Philadelphia). The glycoprotein of Ebola virus is unusual in that it is encoded in two open reading frames. Transcriptional editing is needed to express the transmembrane form that is incorporated into the virion (Sanchez et al. (1996) Proc. Natl. Acad. Sci. USA 93, 3602-3607; Volchkov et al, (1995) Virology 214, 421-430). The unedited form produces a nonstructural secreted glycoprotein (sGP) that is synthesized in large amounts early during the course of infection. Little is known about the biological functions of these proteins and it is not known which antigens significantly contribute to protection and should therefore be used to induce an immune response.

Recent studies using rodent models to evaluate subunit vaccines for Ebola virus infection using recombinant vaccinia virus encoding Ebola virus GP (Gilligan et al., (1997) In Vaccines 97, pp. 87-92. Cold Spring Harbor Laboratory Press, Cold Spring Harbor, N.Y.), or naked DNA constructs expressing either GP or sGP (Xu et al. (1998) Nature Med. 4, 37-42) have demonstrated the protective efficacy of Ebola virus GP in guinea pigs. (All documents cited herein supra and infra are hereby incorporated in their entirety by reference thereto.) Additionally, Ebola virus NP and GP genes expressed from naked DNA vaccines (Vanderzanden et al.,(1998) Virology 246, 134-144) have elicited protective immunity in BALB/c mice. There has been one study that showed protection in nonhuman primates with a high dose DNA prime/high dose adenovirus boost and a 6 pfu challenge. However, this study provides limited benefit for humans or non-human primates because such high dosing is unlikely to be given to humans due to high inherent risks and other factors. So there still exists a need for a human vaccine which is efficacious for protection from Ebola virus infection.

SUMMARY OF THE INVENTION

The present invention satisfies the need discussed above. The present invention relates to a method and composition for use in inducing an immune response which is protective against infection with Ebola virus.

Because the biological functions of the individual Ebola virus proteins were not previously known and the immune mechanisms necessary for preventing and clearing Ebola virus infection were not previously well understood, it was not known which antigens significantly contribute to protection and should therefore be included in an eventual vaccine candidate to induce a protective immune response. However, the inventors have induced protection against Ebola infection in mammals using virus replicon particles (VRPs) expressing the Ebola GP, NP, VP24, VP30, VP35 or VP40 genes. These VRPs and some uses are described in co-pending application Ser. No. 09/337,946 (filed Jun. 22, 1999), the entire contents of which are hereby incorporated by reference.

One embodiment of the present invention entails a DNA fragment encoding each of the Ebola Zaire 1976 GP, NP, VP24, VP30, VP35, and VP40 virion proteins (SEQUENCE ID NOS. 1-7).

Another embodiment provides the DNA fragments of Ebola virion proteins in a recombinant vector. When the vector is an expression vector, the Ebola virion proteins GP, NP, VP24, VP30, VP35, and VP40 are produced. It is preferred that the vector is an alphavirus replicon vector, especially a replicon vector that has the ability to produce the desired protein or peptide in a manner that induces protective B and T cells in vivo in mammals. Any alphavirus vector may be effective, including but not limited to the Venezuelan Equine Encephalitis (VEE) virus, eastern equine encephalitis, western equine encephalitis, Semliki forest and Sindbis. For instance, in a preferred embodiment the VEE replicon vector comprises a VEE virus replicon and a DNA fragment encoding any of the Ebola Zaire 1976 (Mayinga isolate) GP, NP, VP24, VP30, VP35, or VP40 proteins. In another preferred embodiment, the VEE replicon vector comprises a VEE virus replicon and a DNA fragment encoding any of the amino acid sequences set forth in SEQ ID NOs:24-53. The construct can be used as a nucleic acid vaccine or for the production of self replicating RNA. To that end, a self replicating RNA of this invention can comprise the VEE virus replicon and any of the Ebola Zaire 1976 (Mayinga isolate) RNAs encoding the GP, NP, VP24, VP30, VP35, and VP40 proteins described above, or the amino acid sequences set forth in SEQ ID NOs:24-53. The RNA can be used as a vaccine for protection from Ebola infection. When the RNA is packaged, a VEE virus replicon particle is produced.

Another embodiment entails infectious VEE virus replicon particles produced from the VEE virus replicon RNAs described above.

Another embodiment of the invention encompasses peptides that make up cytotoxic T lymphocyte (CTL) epitopes corresponding to Ebola GP, NP, VP24, VP30, VP35, or VP40 proteins. The epitopes may include the sequences identified as SEQ ID NOS:24-53, as described below. A related aspect of this embodiment provides DNA fragments that respectively encode these Ebola peptides. A further embodiment relates to recombinant DNA constructs that express these epitope peptides.

An additional embodiment includes a pharmaceutical composition that includes one or more of these CTL epitope peptides (and preferably one or more of SEQ ID NOs:24-53), in an effective immunogenic amount in a pharmaceutically acceptable carrier and/or adjuvant.

A further embodiment entails an immunological composition for the protection of mammals including humans against *Ebola* virus infection, comprising at least one (but preferably at least two, and more preferably at least three, and most preferably all) of the *Ebola* virus GP, NP, VP24, VP30, VP35, or VP40 proteins. In a related embodiment, the composition may include one or more of the CTL epitopes set forth in SEQ ID NOs: 24-53 (described below).

In a related preferred embodiment, the immunological compositions comprise alphavirus replicon particles (such as, for instance, VEE virus replicon particles) expressing the *Ebola* virus GP, NP, VP24, VP30, VP35, or VP40 proteins, or any combination of different VEE virus replicons each expressing one or more different *Ebola* proteins selected from GP, NP, VP24, VP30, VP35 and VP40. For instance, in a preferred embodiment the composition may include one or more of SEQ ID NOs: 24-53 (described below). In another preferred embodiment, the composition includes at least the VP30, VP35 and VP40 proteins.

An additional embodiment includes vaccines against infection by *Ebola*, comprising virus replicon particles (preferably VEE virus replicon particles) expressing the *Ebola* virus GP, NP, VP24, VP30, VP35, or VP40 proteins, or any combination of different VEE virus replicons each expressing one or more different *Ebola* proteins selected from GP, NP, VP24, VP30, VP35 and VP40. For instance, in a preferred embodiment the *Ebola* VRPs contain one or more of the peptides specified by SEQ ID NOs: 24-53. In a related embodiment, the vaccine may include at a minimum at least one of the *Ebola* proteins selected from GP, NP, VP24, VP30, VP35 and VP40. For instance, in a preferred embodiment the vaccine includes at least the VP30, VP35 and VP40 proteins. In another preferred embodiment, the vaccine may include one or more of SEQ ID NOs: 24-53.

The invention also contemplates methods for inducing in a mammal a cytotoxic T lymphocyte response to the *Ebola* virus GP, NP, VP24, VP30, VP35, or VP40 proteins, or to a peptide comprising at least 6 amino acids thereof. In one version of the method, a recombinant DNA construct is administered to a mammal, such as, for example, a mouse, a guinea pig, a monkey or a human, which a recombinant DNA construct expresses the amino acid sequence of at least one of the *Ebola* virus GP, NP, VP24, VP30, VP35, or VP40 proteins (or a peptide comprising at least 6 amino acids thereof), under such conditions that a protective CTL response is induced in that mammal. In particular, the administered peptides may include one or more of SEQ ID NOs: 24-53. In another version of the method, one of the above-described immunogenic compositions is administered to the mammal, and preferably one that comprises virus replicon particles containing one of the *Ebola* virus GP, NP, VP24, VP30, VP35, or VP40 proteins (or a peptide comprising at least 6 amino acids thereof), or including one of the CTL epitopes set forth in SEQ ID NOs:24-53. In another version of the method, the amino acid sequence of at least one of the *Ebola* virus GP, NP, VP24, VP30, VP35, or VP40 proteins (or a peptide comprising at least 6 amino acids thereof) is administered to a mammal, such as, for example, a mouse, a guinea pig, a monkey or a human, under such conditions that a protective CTL response is induced in that mammal. In particular, the administered peptides may include one or more of SEQ ID NOs: 24-53.

BRIEF DESCRIPTION OF THE DRAWINGS

These and other features, aspects, and advantages of the present invention will become better understood with reference to the following description and appended claims, and accompanying drawings where:

FIGS. 2A, 2B and 2C are schematic representations of the VEE replicon constructs containing *Ebola* genes.

FIG. 3 shows the generation of VEE viral-like particles containing *Ebola* genes.

FIG. 4 is an immunoprecipitation of *Ebola* proteins produced from replicon constructs.

DETAILED DESCRIPTION

Figure 1:
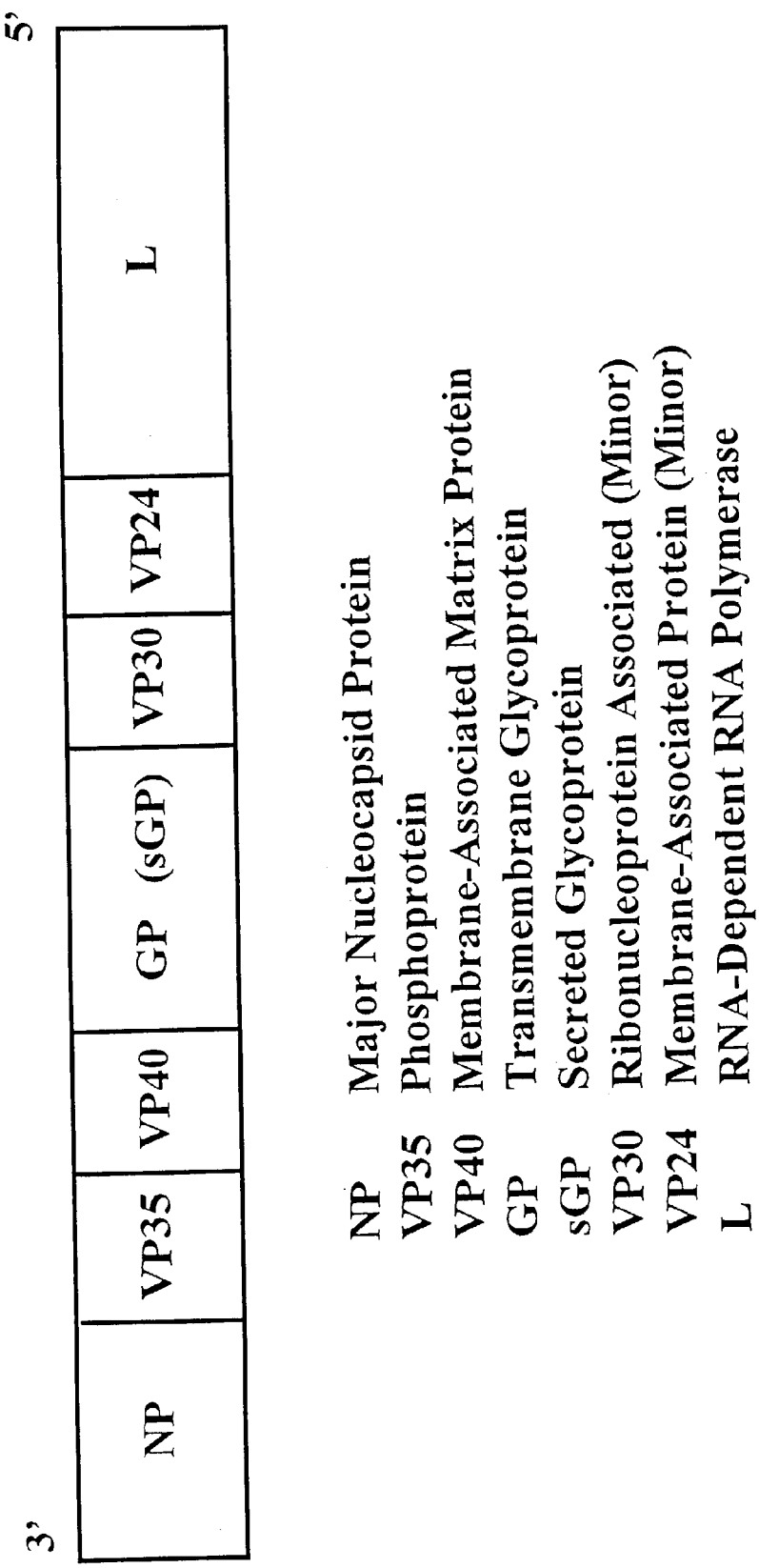
FIG. 1 is a schematic description of the organization of the *Ebola* virus genome.

In the description that follows, a number of terms used in recombinant DNA, virology and immunology are extensively utilized. In order to provide a clearer and consistent understanding of the specification and claims, including the scope to be given such terms, the following definitions are provided.

Filoviruses. The filoviruses (e.g. *Ebola* Zaire 1976) cause acute hemorrhagic fever characterized by high mortality. Humans can contract filoviruses by infection in endemic regions, by contact with imported primates, and by performing scientific research with the virus. However, there currently are no available vaccines or effective therapeutic treatments for filovirus infection in humans. The virions of filoviruses contain seven proteins: a membrane-anchored glycoprotein (GP), a nucleoprotein (NP), an RNA-dependent RNA polymerase (L), and four virion structural proteins (VP24, VP30, VP35, and VP40). Little is known about the biological functions of these proteins and it is not known which antigens significantly contribute to protection and should therefore be used in an eventual vaccine candidate.

Replicon. A replicon is equivalent to a full-length virus from which all of the viral structural proteins have been deleted. A multiple cloning site can be inserted downstream of the 26S promoter into the site previously occupied by the structural protein genes. Virtually any heterologous gene may be inserted into this cloning site. The RNA that is transcribed from the replicon is capable of replicating and expressing viral proteins in a manner that is similar to that seen with the full-length infectious virus clone. However, in lieu of the viral structural proteins, the heterologous antigen is expressed from the 26S promoter in the replicon. This system does not yield any progeny virus particles because there are no viral structural proteins available to package the RNA into particles.

Particles which appear structurally identical to virus particles can be produced by supplying structural protein RNAs in trans for packaging of the replicon RNA. This is typically done with two defective helper RNAs which encode the structural proteins. One helper consists of a full length infectious clone from which the nonstructural protein genes and the glycoprotein genes are deleted. This helper retains only the terminal nucleotide sequences, the promoter for subgenomic mRNA transcription and the sequences for the viral nucleocapsid protein. The second helper is identical to the first except that the nucleocapsid gene is deleted and only the glycoprotein genes are retained. The helper RNAs are transcribed in vitro and are co-transfected with replicon RNA. Because the replicon RNA retains the sequences for packaging by the nucleocapsid protein, and because the helpers lack these sequences, only the replicon RNA is packaged by the viral structural proteins. The packaged replicon particles are released from the host cell and can then be purified and inoculated into animals. The packaged replicon particles will have a tropism similar to the parent virus. The packaged replicon particles will infect cells and initiate a single round of replication, resulting in the expression of only the virus nonstructural proteins and the product of the heterologous gene that was cloned in the place of the virus structural proteins. In the absence of RNA encoding the virus structural proteins, no progeny virus particles can be produced from the cells infected by packaged replicon particles.

Any alphavirus replicon may be effective in this invention, as long as it has the ability to produce the desired protein or peptide in a manner that induces protective B and T cells in vivo in mammals to which it is administered to (such as, for instance, eastern equine encephalitis, western equine encephalitis, Semlike forest, Sindbis and Venezualen Equine Encephalitis).

The VEE virus replicon (Vrep) is a preferred vector system. The Vrep is a genetically reorganized version of the VEE virus genome in which the structural protein genes are replaced with a gene from an immunogen of interest, such as the *Ebola* virus virion proteins. This replicon can be transcribed to produce a self-replicating RNA that can be packaged into infectious particles using defective helper RNAs that encode the glycoprotein and capsid proteins of the VEE virus. Since the packaged replicons do not encode the structural proteins, they are incapable of spreading to new cells and therefore undergo a single abortive round of replication in which large amounts of the inserted immunogen are made in the infected cells. The VEE virus replicon system is described in U.S. patent to Johnston et al., U.S. Pat. No. 5,792,462 issued on Aug. 11, 1998.

Subject. Includes both human, animal, e.g., horse, donkey, pig, mouse, hamster, monkey, chicken, and insect such as mosquito.

In one embodiment, the present invention relates to DNA fragments which encode any of the *Ebola* Zaire 1976 (Mayinga isolate) GP, NP, VP24, VP30, VP35, and VP40 proteins. The GP and NP genes of *Ebola* Zaire were previously sequenced by Sanchez et al. (1993, supra) and have been deposited in GenBank (accession number L11365). A plasmid encoding the VEE replicon vector containing a unique ClaI site downstream from the 26S promoter was described previously (Davis, N. L. et al., (1996) *J. Virol.* 70, 3781-3787; Pushko, P. et al. (1997) *Virology* 239, 389-401). The *Ebola* GP and NP genes from the *Ebola* Zaire 1976 virus were derived from PS64- and PGEM3ZF(−)-based plasmids (Sanchez, A. et al. (1989) *Virology* 170, 81-91; Sanchez, A. et al. (1993) *Virus Res.* 29, 215-240). From these plasmids, the BamHI-EcoRI (2.3 kb) and BamHI-KpnI (2.4 kb) fragments containing the NP and GP genes, respectively, were subcloned into a shuttle vector that had been digested with BamHI and EcoRI (Davis et al. (1996) supra; Grieder, F. B. et al. (1995) *Virology* 206, 994-1006). For cloning of the GP gene, overhanging ends produced by KpnI (in the GP fragment) and EcoRI (in the shuttle vector) were made blunt by incubation with T4 DNA polymerase according to methods known in the art. From the shuttle vector, GP or NP genes were subcloned as ClaI-fragments into the ClaI site of the replicon clone, resulting in plasmids encoding the GP or NP genes in place of the VEE structural protein genes downstream from the VEE 26S promoter.

The VP genes of *Ebola Zaire* were previously sequenced by Sanchez et al. (1993, supra) and have been deposited in GenBank (accession number L11365). The VP genes of *Ebola* used in the present invention were cloned by reverse transcription of RNA from *Ebola*-infected Vero E6 cells and subsequent amplification of viral cDNAs using the polymerase chain reaction. First strand synthesis was primed with oligo dT (Life Technologies). Second strand synthesis and subsequent amplification of viral cDNAs were performed with gene-specific primers (SEQ ID NOS:8-16). The primer sequences were derived from the GenBank deposited sequences and were designed to contain a ClaI restriction site for cloning the amplified VP genes into the ClaI site of the replicon vector. The letters and numbers in bold print indicate *Ebola* gene sequences in the primers and the corresponding location numbers based on the GenBank deposited sequences.

```
VP24:  (1) forward primer is           (SEQ ID NO:8)
    5'-GGGATCGATCTCCAGACACCAAGCAAGACC-3'
           (10,311-10,331)

(2) reverse primer is           (SEQ ID NO:9)
    5'-GGGATCGATGAGTCAGCATATATGAGTTAGCTC-3'
           (11,122-11,145)

VP30:  (1) forward primer is           SEQ ID NO:10)
    5'-CCCATCGATCAGATCTGCGAACCGGTAGAG-3'
           (8408-8430)

(2) reverse primer is           (SEQ ID NO:11)
    5'-CCCATCGATGTACCCTCATCAGACCATGAGC-3'
           (9347-9368)

VP35:  (1) forward primer is           (SEQ ID NO:12)
    5'-GGGATCGATAGAAAAGCTGGTCTAACAAGATGA-3'
           (3110-3133)

(2) reverse primer is           (SEQ ID NO:13)
    5'-CCCATCGATCTCACAAGTGTATCATTAATGTAACGT-3'
           (4218-4244)

VP40:  (1) forward primer is           (SEQ ID NO:14)
    5'-CCCATCGATCCTACCTCGGCTGAGAGAGTG-3'
           (4408-4428)

(2) reverse primer is           (SEQ ID NO:15)
    5'-CCCATCGATATGTTATGCACTATCCCTGAGAAG-3'
           (5495-5518)

VP30 #2:
       (1) forward primer as for VP30 above
       (2) reverse primer is           (SEQ ID NO:16)
    5'-CCCATCGATCTGTTAGGGTTGTATCATACC-3'
```

The *Ebola* virus genes cloned into the VEE replicon were sequenced. Changes in the DNA sequence relative to the sequence published by Sanchez et al. (1993) are described relative to the nucleotide (nt) sequence number from GenBank (accession number L11365).

The nucleotide sequence we obtained for *Ebola* virus GP (SEQ ID NO:1) differed from the GenBank sequence by a transition from A to G at nt 8023. This resulted in a change in the amino acid sequence from Ile to Val at position 662 (SEQ ID NO: 17).

The nucleotide sequence we obtained for *Ebola* virus NP (SEQ ID NO:2) differed from the GenBank sequence at the following 4 positions: insertion of a C residue between nt 973 and 974, deletion of a G residue at nt 979, transition from C to T at nt 1307, and a transversion from A to C at nt 2745. These changes resulted in a change in the protein sequence from Arg to Glu at position 170 and a change from Leu to Phe at position 280 (SEQ ID NO: 18).

The *Ebola* virus VP24 nucleotide sequence (SEQ ID NO:3) differed from the GenBank sequence at 6 positions, resulting in 3 nonconservative changes in the amino acid sequence. The changes in the DNA sequence of VP24 consisted of a transversion from G to C at nt 10795, a transversion from C to G at nt 10796, a transversion from T to A at nt 10846, a transversion from A to T at nt 10847, a transversion from C to G at nt 11040, and a transversion from C to G at nt 11041. The changes in the amino acid sequence of VP24 consisted of a Cys to Ser change at position 151, a Leu to His change at position 168, and a Pro to Gly change at position 233 (SEQ ID NO: 19).

Two different sequences for the *Ebola* virus VP30 gene, VP30 and VP30#2 (SEQ ID NOS: 4 and 7) are included. Both of these sequences differ from the GenBank sequence by the insertion of an A residue in the upstream noncoding sequence between nt 8469 and 8470 and an insertion of a T residue between nt 9275 and 9276 that results in a change in the open reading frame of VP30 and VP30#2 after position 255 (SEQ ID NOS: 20 and 23). As a result, the C-terminus of the VP30 protein differs significantly from that previously reported. In addition to these 2 changes, the VP30#2 nucleic acid in SEQ ID NO:7 contains a conservative transition from T to C at nt 9217. Because the primers originally used to clone the VP30 gene into the replicon were designed based on the GenBank sequence, the first clone that we constructed (SEQ ID NO: 4) did not contain what we believe to be the authentic C-terminus of the protein. Therefore, in the absence of the VP30 stop codon, the C-terminal codon was replaced with 37 amino acids derived from the vector sequence. The resulting VP30 construct therefore differed from the GenBank sequence in that it contained 32 amino acids of VP30 sequence (positions 256 to 287, SEQ ID NO:20) and 37 amino acids of irrelevant sequence (positions 288 to 324, SEQ ID NO:20) in the place of the C-terminal 5 amino acids reported in GenBank. However, inclusion of 37 amino acids of vector sequence in place of the C-terminal amino acid (Pro, SEQ ID NO: 23) did not inhibit the ability of the protein to serve as a protective antigen in BALB/c mice. We have also determined that a VEE replicon construct, which contains the authentic C-terminus of VP30 (VP30#2, SEQ ID NO: 23), protects mice against a lethal *Ebola* challenge.

The nucleotide sequence for *Ebola* virus VP35 (SEQ ID NO:5) differed from the GenBank sequence by a transition from T to C at nt 4006, a transition from T to C at nt 4025, and an insertion of a T residue between nt 4102 and 4103. These sequence changes resulted in a change from a Ser to a Pro at position 293 and a change from Phe to Ser at position 299 (SEQ ID NO: 21). The insertion of the T residue resulted in a change in the open reading frame of VP35 from that previously reported by Sanchez et al. (1993) following amino acid number 324. As a result, *Ebola* virus VP35 encodes a protein of 340 amino acids, where amino acids 325 to 340 (SEQ ID NO: 21) differ from and replace the C-terminal 27 amino acids of the previously published sequence.

Sequencing of VP30 and VP35 was also performed on RT/PCR products from RNA derived from cells that were infected with *Ebola* virus 1976, *Ebola* virus 1995 or the mouse-adapted *Ebola* virus. The changes noted above for the Vrep constructs were also found in these *Ebola* viruses. Thus, we believe that these changes are real events and not artifacts of cloning.

The *Ebola* virus VP40 nucleotide sequence (SEQ ID NO:6) differed from the GenBank sequence by a transversion from a C to G at nt 4451 and a transition from a G to A at nt 5081. These sequence changes did not alter the protein sequence of VP40 (SEQ ID NO: 22) from that of the published sequence.

Each of the *Ebola* virus genes were individually inserted into a VEE virus replicon vector. The VP24, VP30, VP35, and VP40 genes of *Ebola Zaire* 1976 (Mayinga isolate) were cloned by reverse transcription of RNA from *Ebola*-infected Vero E6 cells and viral cDNAs were amplified using the polymerase chain reaction. The *Ebola Zaire* 1976 (Mayinga isolate) GP and NP genes were obtained from plasmids already containing these genes (Sanchez, A. et al., (1989) *Virology* 170, 81-91; Sanchez, A. et al.,(1993) *Virus Res.* 29, 215-240) and were subcloned into the VEE replicon vector.

After characterization of the *Ebola* gene products expressed from the VEE replicon constructs in cell culture, these constructs were packaged into infectious VEE virus replicon particles (VRPs) and subcutaneously injected into BALB/c and C57BL/6 mice. As controls in these experiments, mice were also immunized with a VEE replicon expressing Lassa nucleoprotein (NP) as an irrelevant control antigen, or injected with PBS buffer alone. The results of this study demonstrate that VRPs expressing the *Ebola* GP, NP, VP24, VP30, VP35 or VP40 genes induced protection in mice and may reasonably to expected to provide protection in humans.

DNA or polynucleotide sequences to which the invention also relates include sequences of at least about 6 nucleotides, preferably at least about 8 nucleotides, more preferably at least about 10-12 nucleotides, most preferably at least about 15-20 nucleotides corresponding, i.e., homologous to or complementary to, a region of the *Ebola* nucleotide sequences described above. Preferably, the sequence of the region from which the polynucleotide is derived is homologous to or complementary to a sequence which is unique to the *Ebola* genes. Whether or not a sequence is unique to the *Ebola* gene can be determined by techniques known to those of skill in the art. For example, the sequence can be compared to sequences in databanks, e.g., GenBank and compared by DNA:DNA hybridization. Regions from which typical DNA sequences may be derived include but are not limited to, for example, regions encoding specific epitopes, as well as non-transcribed and/or non-translated regions.

The derived polynucleotide is not necessarily physically derived from the nucleotide sequences shown in SEQ ID NO:1-7, but may be generated in any manner, including for example, chemical synthesis or DNA replication or reverse transcription or transcription, which are based on the information provided by the sequence of bases in the region(s) from which the polynucleotide is derived. In addition, combinations of regions corresponding to that of the designated sequence may be modified in ways known in the art to be consistent with an intended use. The sequences of the present invention can be used in diagnostic assays such as hybridization assays and polymerase chain reaction assays, for example, for the discovery of other *Ebola* sequences.

In another embodiment, the present invention relates to a recombinant DNA molecule that includes a vector and a DNA sequence as described above. The vector can take the form of a plasmid, a eukaryotic expression vector such as pcDNA3.1, pRcCMV2, pZeoSV2,or pCDM8, which are available from Invitrogen, or a virus vector such as baculovirus vectors, retrovirus vectors or adenovirus vectors, alphavirus vectors, and others known in the art.

In a further embodiment, the present invention relates to host cells stably transformed or transfected with the above-described recombinant DNA constructs. The host cell can be prokaryotic (for example, bacterial), lower eukaryotic (for example, yeast or insect) or higher eukaryotic (for example, all mammals, including but not limited to mouse and human). Both prokaryotic and eukaryotic host cells may be used for expression of the desired coding sequences when appropriate control sequences which are compatible with the designated host are used.

Among prokaryotic hosts, *E. coli* is the most frequently used host cell for expression. General control sequences for prokaryotes include promoters and ribosome binding sites.

Transfer vectors compatible with prokaryotic hosts are commonly derived from a plasmid containing genes conferring ampicillin and tetracycline resistance (for example, pBR322) or from the various pUC vectors, which also contain sequences conferring antibiotic resistance. These antibiotic resistance genes may be used to obtain successful transformants by selection on medium containing the appropriate antibiotics. Please see e.g., Maniatis, Fitsch and Sambrook, *Molecular Cloning; A Laboratory Manual* (1982) or *DNA Cloning*, Volumes I and II (D. N. Glover ed. 1985) for general cloning methods. The DNA sequence can be present in the vector operably linked to sequences encoding an IgG molecule, an adjuvant, a carrier, or an agent for aid in purification of *Ebola* proteins, such as glutathione S-transferase.

In addition, the *Ebola* virus gene products can also be expressed in eukaryotic host cells such as yeast cells and mammalian cells. *Saccharomyces cerevisiae, Saccharomyces carlsbergensis,* and *Pichia pastoris* are the most commonly used yeast hosts. Control sequences for yeast vectors are known in the art. Mammalian cell lines available as hosts for expression of cloned genes are known in the art and include many immortalized cell lines available from the American Type Culture Collection (ATCC), such as CHO cells, Vero cells, baby hamster kidney (BHK) cells and COS cells, to name a few. Suitable promoters are also known in the art and include viral promoters such as that from SV40, Rous sarcoma virus (RSV), adenovirus (ADV), bovine papilloma virus (BPV), and cytomegalovirus (CMV). Mammalian cells may also require terminator sequences, poly A addition sequences, enhancer sequences which increase expression, or sequences which cause amplification of the gene. These sequences are known in the art.

The transformed or transfected host cells can be used as a source of DNA sequences described above. When the recombinant molecule takes the form of an expression system, the transformed or transfected cells can be used as a source of the protein described below.

In another embodiment, the present invention relates to *Ebola* virion proteins such as GP having an amino acid sequence corresponding to SEQ ID NO:17 encompassing 676 amino acids, NP, having an amino acid sequence corresponding to SEQ ID NO:18 encompassing 739 amino acids, VP24, having an amino acid sequence corresponding to SEQ ID NO:19 encompassing 251 amino acids, VP30, having an amino acid sequence corresponding SEQ ID NO:20 encompassing 324 amino acids, VP35, having an amino acid sequence corresponding to SEQ ID NO:21 encompassing 340 amino acids, and VP40, having an amino acid sequence corresponding to SEQ ID NO:22, encompassing 326 amino acids, and VP30#2, having an amino acid sequence corresponding to SEQ ID NO:23 encompassing 288 amino acids, or any allelic variation of these amino acid sequences. By allelic variation is meant a natural or synthetic change in one or more amino acids which occurs between different serotypes or strains of *Ebola* virus and does not affect the antigenic properties of the protein. There are different strains of *Ebola* (Zaire 1976, Zaire 1995, Reston, Sudan, and Ivory Coast). The NP and VP genes of all these different viruses have not been sequenced. It would be expected that these proteins would have homology among different strains and that vaccination against one *Ebola* virus strain might afford cross protection to other *Ebola* virus strains.

A polypeptide or amino acid sequence derived from any of the amino acid sequences in SEQ ID NO:17, 18, 19, 20, 21, 22, and 23 refers to a polypeptide having an amino acid sequence identical to that of a polypeptide encoded in the sequence, or a portion thereof wherein the portion consists of at least 2-5 amino acids, preferably at least 8-10 amino acids, and more preferably at least 11-15 amino acids, or which is immunologically identifiable with a polypeptide encoded in the sequence.

A recombinant or derived polypeptide is not necessarily translated from a designated nucleic acid sequence, or the DNA sequence found in GenBank accession number L11365. It may be generated in any manner, including for example, chemical synthesis, or expression from a recombinant expression system.

When the DNA or RNA sequences described above are in a replicon expression system, such as the VEE replicon described above, the proteins can be expressed in vivo. The DNA sequence for any of the GP, NP, VP24, VP30, VP35, and VP40 virion proteins can be cloned into the multiple cloning site of a replicon such that transcription of the RNA from the replicon yields an infectious RNA encoding the *Ebola* protein or proteins of interest (see FIGS. 2A, 2B and 2C). The replicon constructs include *Ebola* virus GP (SEQ ID NO:1) cloned into a VEE replicon (VRepEboGP), *Ebola* virus NP (SEQ ID NO:2) cloned into a VEE replicon (VRepEboNP), *Ebola* virus VP24 (SEQ ID NO:3) cloned into a VEE replicon (VRepEboVP24), *Ebola* virus VP30 (SEQ ID NO:4) or VP30#2 (SEQ ID NO:7) cloned into a VEE replicon (VRepEboVP30 or VRepEboVP30(#2)), *Ebola* virus VP35 (SEQ ID NO:5) cloned into a VEE replicon (VRepEboVP35), and *Ebola* virus VP40 (SEQ ID NO:6) cloned into a VEE replicon (VRepEboVP40). The replicon DNA or RNA can be used as a vaccine for inducing protection against infection with *Ebola*.

Use of helper RNAs containing sequences necessary for packaging of the viral replicon transcripts will result in the production of virus-like particles containing replicon RNAs (FIG. 3). These packaged replicons will infect host cells and initiate a single round of replication resulting in the expression of the *Ebola* proteins in the infected cells. The packaged replicon constructs (i.e. VEE virus replicon particles, VRP) include those that express *Ebola* virus GP (EboGPVRP), *Ebola* virus NP (EboNPVRP), *Ebola* virus VP24 (EboVP24VRP), *Ebola* virus VP30 (EboVP30VRP or EboVP30VRP(#2)), *Ebola* virus VP35 (EboVP35VRP), and *Ebola* virus VP40 (EboVP40VRP).

In another embodiment, the present invention relates to RNA molecules resulting from the transcription of the constructs described above. The RNA molecules can be prepared by in vitro transcription using methods known in the art and described in the Examples below. Alternatively, the RNA molecules can be produced by transcription of the constructs in vivo, and isolating the RNA. These and other methods for obtaining RNA transcripts of the constructs are known in the art. Please see Current *Protocols in Molecular Biology.* Frederick M. Ausubel et al. (eds.), John Wiley and Sons, Inc. The RNA molecules can be used, for example, as a direct RNA vaccine, or to transfect cells along with RNA from helper plasmids, one of which expresses VEE glycoproteins and the other VEE capsid proteins, as described above, in order to obtain replicon particles.

In a further embodiment, the present invention relates to a method of producing the recombinant or fusion protein which includes culturing the above-described host cells under conditions such that the DNA fragment is expressed and the recombinant or fusion protein is produced thereby. The recombinant or fusion protein can then be isolated using methodology well known in the art. The recombinant or fusion protein can be used as a vaccine for immunity against infection with *Ebola* or as a diagnostic tool for detection of *Ebola* infection.

In another embodiment, the present invention relates to antibodies specific for the above-described recombinant proteins (or polypeptides). For instance, an antibody can be raised against a peptide having the amino acid sequence of any of SEQ ID NO:17-25, or against a portion thereof of at least 10 amino acids, preferably, 11-15 amino acids. Persons with ordinary skill in the art using standard methodology can raise monoclonal and polyclonal antibodies to the protein(or polypeptide) of the present invention, or a unique portion thereof. Materials and methods for producing antibodies are well known in the art (see for example Goding, In *Monoclonal Antibodies: Principles and Practice,* Chapter 4, 1986).

In another embodiment, the present invention relates to an Ebola vaccine comprising VRPs that express one or more of the *Ebola* proteins described above. The vaccine is administered to a subject wherein the replicon is able to initiate one round of replication producing the *Ebola* proteins to which a protective immune response is initiated in said subject.

It is likely that the protection afforded by these genes is due to both the humoral (antibodies (Abs)) and cellular (cytotoxic T cells (CTLs)) arms of the immune system. Protective immunity induced to a specific protein may comprise humoral immunity, cellular immunity, or both. The only *Ebola* virus protein known to be on the outside of the virion is the GP. The presence of GP on the virion surface makes it a likely target for GP-specific Abs that may bind either extracellular virions or infected cells expressing GP on their surfaces. Serum transfer studies in this invention demonstrate that Abs that recognize GP protect mice against lethal *Ebola* virus challenge.

In contrast, transfer of Abs specific for NP, VP24, VP30, VP35, or VP40 did not protect mice against lethal *Ebola* challenge. This data, together with the fact that these are internal virion proteins that are not readily accessible to Abs on either extracellular virions or the surface of infected cells, suggest that the protection induced in mice by these proteins is mediated by CTLs.

CTLs can bind to and lyse virally infected cells. This process begins when the proteins produced by cells are routinely digested into peptides. Some of these peptides are bound by the class I or class II molecules of the major histocompatability complex (MHC), which are then transported to the cell surface. During virus infections, viral proteins produced within infected cells also undergo this process. CTLs that have receptors that bind to both a specific peptide and the MHC molecule holding the peptide lyse the peptide-bearing cell, thereby limiting virus replication. Thus, CTLs are characterized as being specific for a particular peptide and restricted to a class I or class II MHC molecule.

CTLs may be induced against any of the *Ebola* virus proteins, as all of the viral proteins are produced and digested within the infected cell. Thus, protection to *Ebola* virus involves CTLs against GP, NP, VP24, VP30, VP35, and/or VP40. It is especially noteworthy that the VP proteins varied in their protective efficacy when tested in genetically inbred mice that differ at the MHC locus. This, together with the inability to demonstrate a role for Abs in protection induced by the VP proteins and the data in Table A below, demonstrates a role for CTLs. Thus, in this invention a vaccine may include several *Ebola* virus proteins (e.g., at least two), or several CTL epitopes (e.g., at least two), capable of inducing broad protection to different *Ebola* viruses in outbred populations (e.g. people). To that end, the inventors have identified 18 sequences recognized by CTLs, as determined initially by measuring gamma interferon production by intracellular cytokine staining and gamma interferon secretion by the ELISpot assay. The ability to lyse cells was measured in chromium release assays and protection was evaluated by adoptive transfer of cells into Ebola-naïve mice. Where sequence information is available, the conservation of these CTL epitopes in other *Ebola* viruses is noted in Table A. Conserved sequences should be capable of inducing protective CTLs to each of the viruses in which the sequence is present.

The identified CTL epitopes are:

*Ebola* virus NP SEQ ID NO:24, SEQ ID NO:26, SEQ ID NO:27, and SEQ ID NO:28;

*Ebola* virus GP SEQ ID NO:29 (encompassing YFGPAAEGI, SEQ ID NO:42);

*Ebola* virus VP24 SEQ ID NO:25 (encompassing KFINKLDAL, SEQ ID NO:43), SEQ ID NO:30 (encompassing NYNGLLSSI, SEQ ID NO:44), and SEQ ID NO:31 (encompassing PGPAKFSLL, SEQ ID NO:45);

*Ebola* virus VP30 SEQ ID NO:32 (encompassing LSLLCETHLR, SEQ ID NO:46), and SEQ ID NO:33 (encompassing MFITAFLNI, SEQ ID NO:47);

*Ebola* virus VP35 SEQ ID NO:34, SEQ ID NO:35, and SEQ ID NO:36; and

*Ebola* virus VP40 SEQ ID NO:37 (encompassing EFVLPPVQL, SEQ ID NO:48), SEQ ID NO:38 (encompassing FLVPPV, SEQ ID NO:49 and QYFTFDLTALK, SEQ ID NO:50), SEQ ID NO:39 (encompassing TSPEKIQAI, SEQ ID NO:51); SEQ ID NO:40 (encompassing RIGNQAFL, SEQ ID NO:52), and SEQ ID NO:41 (encompassing QAFLQEFV, SEQ ID NO:53).

See Table A below.

Testing to identify the role of CTLs in protection was performed by obtaining CTLs from mice, expanding them in vitro, and transferring the cells into an unvaccinated mouse of the same genetic background. Several hours later, the recipient mice were challenged with 10-1000 pfu of mouse-adapted *Ebola* virus. They were observed for signs of illness for 28 days. Control animals received no cells or cells that were not specific for *Ebola* virus. Testing of the cells in vitro indicated that they were CD8+, a marker indicating class I-restriction. The inventors were able to demonstrate that CTLs to these sequences protected at least 80% of recipient mice from challenge. In all of our examples, the ability to lyse peptide-pulsed target cells has predicted protection in mice receiving those cells.

TABLE A

Ebola Virus Epitopes Recognized by Murine CD8 + T cells

| Protein[a] | Epitope[b] | % INF-γ ICC[c] | INF-γ ELISpot[d] | $^{51}$Cr[e] | Protective[f] | Restriction[g] | Conserved Strains[h] |
|---|---|---|---|---|---|---|---|
| GP | WIPYFGPAAEGIYTE (SEQ ID 29) | 0.40/0.08 | Y | Neg | IP | H-2$^b$ | R,G |
| NP | VYQVNNLEEIC (SEQ ID 24) | 1.06/0.11 | Y | 55.6 | Yes | H-2$^b$ | G |
|  | GQFLFASL (SEQ ID 26) | 0.88/0.11 | Y | 45 | Yes | H-2$^b$ | S,G |
|  | DAVLYYHMM (SEQ ID 27) | 0.99/0.11 | Y | 40.6 | Yes | H-2$^b$ | G |
|  | SFKAALSSL (SEQ ID 28) | 0.63/0.04 | Y | 38.8 | Yes | H-2$^d$ |  |

TABLE A-continued

Ebola Virus Epitopes Recognized by Murine CD8 + T cells

| Protein[a] | Epitope[b] | % INF-γ ICC[c] | INF-γ ELISpot[d] | $^{51}$Cr[e] | Protective[f] | Restriction[g] | Conserved Strains[h] |
|---|---|---|---|---|---|---|---|
| VP24 | NIL<u>KFINKLDAL</u>HVV (SEQ ID 25) | 0.52/0.09 | Y | 45.9 | Yes | H-2$^d$ | G |
|  | N<u>YNGLLSSI</u>EGTQN (SEQ ID 30) | 0.38/0.09 | Y | 50.6 | Yes | H-2$^d$ | R,G |
|  | RMK<u>PGPAKFSLL</u>HESTLKAFTQGSS (SEQ ID 31) | 3.34/0.09 | Y | 43.2 | Yes* | H-2$^d$ | R,G |
| VP30 | FSKSQ<u>LSLLCETHLR</u> (SEQ ID 32) | 0.45/0.15 | N | 47.3 | Yes* | H-2$^b$ |  |
|  | DLQSL<u>IMFITAFLNI</u> (SEQ ID 33) | 0.7/0.15 | N | ND | Yes* | H-2$^b$ |  |
| VP35 | RNIMYDHL (SEQ ID 34) | 1.53/0.22 | Y | 87.4 | Yes | H-2$^b$ |  |
|  | MVAKYDLL (SEQ ID 35) | 1.63/0.22 | N | 78.9 | Yes | H-2$^b$ | R |
|  | CDIENNPGL (SEQ ID 36) | 1.99/0.15 | N | 80.4 | Yes | H-2$^b$ |  |
| VP40 | AFLQ<u>EFVLPPVQL</u>PQ (SEQ ID 37) | 0.45/0.22 | ND | ND | IP | H-2$^d$ |  |
|  | <u>FVLPPVQLPQYFTFDLTALK</u> (SEQ ID 38) | 0.41/0.22 | ND | 38 | Yes* | H-2$^d$ |  |
|  | KSGKKGNSADL<u>TSPEKIQAI</u>MTSLQDFKIV (SEQ ID 39) | 0.6/0.22 | N | 36.4 | IP | H-2$^d$ |  |
|  | PLRLL<u>RIGNQAFLQE</u> (SEQ ID 40) | 0.7/0.05 | N | 52.8 | Yes | H-2$^b$ |  |
|  | RIGN<u>QAFLQEFVLPP</u> (SEQ ID 41) | 0.38/0.05 | N | 46.7 | IP | H-2$^b$ |  |

[a]Proteins are from Ebola Zaire '76 virus: GP, glycoprotein, NP, nucleoprotein, or the virion proteins VP24, VP30, VP35 or VP40.
[b]Epitope, indicates peptide sequence(s) tested in the T cell assays. Underlined regions are presumed minimum epitopes based on binding motifs, algorithm predictions and/or demonstrated effects based on synthesis of shorter peptides.
[c]ICC data is % of CD8 that are INF-γ positive and CD8 positive/background
[d]IFN-γ ELISpot assays indicated (Y, yes; N, no) presence of secreted interferon-γ.
[e]$^{51}$Cr data is specific lysis at the 25:1 E:T ratio.
[f]Protection observed in 100% of naive mice receiving CTLs specific for the designated epitopes, except where marked with *, in which cases protection of 80–90% was observed. IP, in progress (data within 2 weeks).
[g]Restriction indicates the major histocompatability type for which lysis was observed. H-2$^b$ mice are C57B1/6 and H-2$^d$are Balb/c.
[h]Conserved strains: underlined sequences representing epitopes are identical in Sudan, Gabon and Reston Ebola viruses as indicated by S, G or R, respectively.
ND, not determined In another embodiment, the invention relates to a vaccine against *Ebola* infection including at least one of these CTL epitope sequences, and preferably at least one CTL epitope having the amino acid sequence of SEQ ID NOs:24-53. Preferably, the vaccine includes at least two of the CTL epitope sequences, more preferably at least three, more preferably at least four, more preferably at least five, and more preferably all of the sequences. As shown in the examples below, protection is increased as the number of CTL epitopes in the immunogenic composition or vaccine is increased, and also as the number of epitopes from different *Ebola* proteins is increased.

In another embodiment, the vaccine includes a CTL epitope sequence from at least two different proteins selected from the group consisting of GP, NP, VP24, VP30, VP35 and VP40. More preferably, the vaccine includes a CTL epitope sequence from at least three different proteins from that group, more preferably at least four, more preferably at least five, and most preferably includes at least one CTL epitope sequence from each of the six proteins. The CTL epitopes may have the amino acid sequences as set forth in SEQ ID NOs:24-53. It is noted that administering the GP peptide alone may prevent the induction of protective antibodies, which may be undesirable.

In a further vaccine embodiment, the vaccine comprises virus replicon particles (preferably VEE virus replicon particles but other alphavirus replicon particles will do as described above) expressing the *Ebola* virus GP, NP, VP24, VP30, VP35, or VP40 proteins, or any combination of different VEE virus replicons each expressing one or more different *Ebola* proteins selected from GP, NP, VP24, VP30, VP35 and VP40. For instance, in a preferred embodiment the *Ebola* VRPs express one or more of the peptides specified by SEQ ID NOs: 24-53.

In another vaccine embodiment, the vaccine may include at a minimum at least one of the *Ebola* proteins selected from GP, NP, VP24, VP30, VP35 and VP40, but preferably contains at least two, more preferably at least three, more preferably at least four, more preferably at least five, and most preferably all of them. It is noted again that administering the GP peptide alone may prevent the induction of protective antibodies, which may be undesirable. For instance, in a preferred embodiment the vaccine includes at least the VP30, VP35 and VP40 proteins. In another preferred embodiment, the vaccine may include one or more of SEQ ID NOs: 24-53.

When considering which type of vaccine may be most effective for an individual, it is noted that the same protective response could be induced by the peptide or the full protein produced from the VRPs. Production of the peptide intracellularly is generally preferred because it is usually (but not always) more effective than providing it extracellularly. Thus, vaccines containing VRPs may be preferred because the VRPs infect cells and therefore achieve intracellular production.

Such vaccines might be delivered as synthetic peptides, or as fusion proteins, alone or co-administered with cytokines and/or adjuvants or carriers safe for human use, e.g. aluminum hydroxide, to increase immunogenicity. In addition, sequences such as ubiquitin can be added to increase antigen processing for more effective CTL responses.

In yet another embodiment, the present invention relates to a method for providing immunity against *Ebola* virus, said method comprising administering one or more VRPs expressing any combination of the GP, NP, VP24, VP30 or VP30#2, VP35 and VP40 *Ebola* proteins to a subject such that a protective immune reaction is generated. In another related embodiment, the method may entail administering one or more VRPs expressing any combination of the peptides designated SEQ ID NOs:24-53, or simply one or more of the peptides designated SEQ ID NOs:24-53.

Vaccine formulations of the present invention comprise an immunogenic amount of a VRP, such as for example EboVP24VRP described above, or, for a multivalent vaccine, a combination of replicons, in a pharmaceutically acceptable carrier. An "immunogenic amount" is an amount of the VRP(s) sufficient to evoke an immune response in the subject to which the vaccine is administered. An amount of from about $10^4$-$10^8$ focus-forming units per dose is suitable, depending upon the age and species of the subject being treated. The subject may be inoculated 2-3 times. Exemplary pharmaceutically acceptable carriers include, but are not limited to, sterile pyrogen-free water and sterile pyrogen-free physiological saline solution.

Administration of the VRPs disclosed herein may be carried out by any suitable means, including parenteral injection (such as intraperitoneal, subcutaneous, or intramuscular injection), in ovo injection of birds, orally, or by topical application of the virus (typically carried in a pharmaceutical formulation) to an airway surface. Topical application of the virus to an airway surface can be carried out by intranasal administration (e.g., by use of dropper, swab, or inhaler which deposits a pharmaceutical formulation intranasally). Topical application of the virus to an airway surface can also be carried out by inhalation administration, such as by creating respirable particles of a pharmaceutical formulation (including both solid particles and liquid particles) containing the replicon as an aerosol suspension, and then causing the subject to inhale the respirable particles. Methods and apparatus for administering respirable particles of pharmaceutical formulations are well known, and any conventional technique can be employed. Oral administration may be in the form of an ingestable liquid or solid formulation.

When the replicon RNA or DNA is used as a vaccine, the replicon RNA or DNA can be administered directly using techniques such as delivery on gold beads (gene gun), delivery by liposomes, or direct injection, among other methods known to people in the art. Any one or more DNA constructs or replicating RNA described above can be use in any combination effective to elicit an immunogenic response in a subject. Generally, the nucleic acid vaccine administered may be in an amount of about 1-5 ug of nucleic acid per dose and will depend on the subject to be treated, capacity of the subject's immune system to develop the desired immune response, and the degree of protection desired. Precise amounts of the vaccine to be administered may depend on the judgement of the practitioner and may be peculiar to each subject and antigen.

The vaccine may be given in a single dose schedule, or preferably a multiple dose schedule in which a primary course of vaccination may be with 1-10 separate doses, followed by other doses given at subsequent time intervals required to maintain and or reinforce the immune response, for example, at 1-4 months for a second dose, and if needed, a subsequent dose(s) after several months. Examples of suitable immunization schedules include: (i) 0, 1 months and 6 months, (ii) 0, 7 days and 1 month, (iii) 0 and 1 month, (iv) 0 and 6 months, (v) 0, 1 and 2 months, or other schedules sufficient to elicit the desired immune responses expected to confer protective immunity, or reduce disease symptoms, or reduce severity of disease.

In a further embodiment, the present invention relates to a method of detecting the presence of antibodies against Ebola virus in a sample. Using standard methodology well known in the art, a diagnostic assay can be constructed by coating on a surface (i.e. a solid support for example, a microtitration plate, a membrane (e.g. nitrocellulose membrane) or a dipstick), all or a unique portion of any of the Ebola proteins described above or any combination thereof, and contacting it with the serum of a person or animal suspected of having Ebola. The presence of a resulting complex formed between the Ebola protein(s) and serum antibodies specific therefor can be detected by any of the known methods common in the art, such as fluorescent antibody spectroscopy or colorimetry. This method of detection can be used, for example, for the diagnosis of Ebola infection and for determining the degree to which an individual has developed virus-specific antibodies after administration of a vaccine.

In yet another embodiment, the present invention relates to a method for detecting the presence of Ebola virion proteins in a sample. Antibodies against GP, NP, and the VP proteins could be used for diagnostic assays. Using standard methodology well known in the art, a diagnostics assay can be constructed by coating on a surface (i.e. a solid support, for example, a microtitration plate or a membrane (e.g. nitrocellulose membrane)), antibodies specific for any of the Ebola proteins described above, and contacting it with serum or a tissue sample of a person suspected of having Ebola infection. The presence of a resulting complex formed between the protein or proteins in the serum and antibodies specific therefor can be detected by any of the known methods common in the art, such as fluorescent antibody spectroscopy or colorimetry. This method of detection can be used, for example, for the diagnosis of Ebola virus infection.

In another embodiment, the present invention relates to a diagnostic kit which contains any combination of the Ebola proteins described above and ancillary reagents that are well known in the art and that are suitable for use in detecting the presence of antibodies to Ebola in serum or a tissue sample. Tissue samples contemplated can be from monkeys, humans, or other mammals.

In yet another embodiment, the present invention relates to DNA or nucleotide sequences for use in detecting the presence of Ebola virus using the reverse transcription-polymerase chain reaction (RT-PCR). The DNA sequence of the present invention can be used to design primers which specifically bind to the viral RNA for the purpose of detecting the presence of Ebola virus or for measuring the amount of Ebola virus in a sample. The primers can be any length ranging from 7 to 400 nucleotides, preferably at least 10 to 15 nucleotides, or more preferably 18 to 40 nucleotides. Reagents and controls necessary for PCR reactions are well known in the art. The amplified products can then be analyzed for the presence of viral sequences, for example by gel fractionation, with or without hybridization, by radiochemistry, and immunochemistry techniques.

In yet another embodiment, the present invention relates to a diagnostic kit which contains PCR primers specific for Ebola virus and ancillary reagents for use in detecting the presence or absence of Ebola in a sample using PCR. Samples contemplated can be obtained from human, animal, e.g., horse, donkey, pig, mouse, hamster, monkey, or other mammals, birds, and insects, such as mosquitoes.

The following examples are included to demonstrate preferred embodiments of the invention. It should be appreciated by those of skill in the art that the techniques disclosed in the examples which follow represent techniques discovered by the inventors and thought to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

The following MATERIALS AND METHODS were used in the examples that follow.

Cells Lines and Viruses

BHK (ATCC CCL 10), Vero 76 (ATCC CRL 1587), and Vero E6 (ATCC CRL 1586) cell lines were maintained in minimal essential medium with Earle's salts, 5-10% fetal bovine serum, and 50 □g/mL gentamicin sulfate. For CTL assays, EL4 (ATCC TIB39), L5178Y (ATCC CRL 1723) and P815 (ATCC TIB64) were maintained in Dulbecco's minimal essential medium supplemented with 5-10% fetal bovine serum and antibiotics.

A stock of the Zaire strain of *Ebola* virus originally isolated from a patient in the 1976 outbreak (Mayinga) and passaged intracerebrally 3 times in suckling mice and 2 times in Vero cells was adapted to adult mice through serial passage in progressively older suckling mice (Bray et al., (1998) *J. Infect. Dis.* 178, 651-661). A plaque-purified ninth-mouse-passage isolate which was uniformly lethal for adult mice ("mouse-adapted virus") was propagated in Vero E6 cells, aliquotted, and used in all mouse challenge experiments and neutralization assays.

A stock of the Zaire strain of *Ebola* 1976 virus was passaged spleen to spleen in strain 13 guinea pigs four times. This guinea pig-adapted strain was used to challenge guinea pigs.

Construction and Packaging of Recombinant VEE Virus Replicons (VRPs)

Replicon RNAs were packaged into VRPs as described (Pushko et al., 1997, supra). Briefly, capped replicon RNAs were produced in vitro by T7 run-off transcription of NotI-digested plasmid templates using the RiboMAX T7 RNA polymerase kit (Promega). BHK cells were co-transfected with the replicon RNAs and the 2 helper RNAs expressing the structural proteins of the VEE virus. The cell culture supernatants were harvested approximately 30 hours after transfection and the replicon particles were concentrated and purified by centrifugation through a 20% sucrose cushion. The pellets containing the packaged replicon particles were suspended in PBS and the titers were determined by infecting Vero cells with serial dilutions of the replicon particles and enumerating the infected cells by indirect immunofluorescence with antibodies specific for the *Ebola* proteins.

Immunoprecipitation of *Ebola* Virus Proteins Expressed from VEE Virus Replicons BHK cells were transfected with either the *Ebola* virus GP, NP, VP24, VP30, VP35, or VP40 replicon RNAs. At 24 h post-transfection, the culture medium was replaced with minimal medium lacking cysteine and methionine, and proteins were labeled for 1 h with $^{35}$S-labeled methionine and cysteine. Cell lysates or supernatants (supe) were collected and immunoprecipitated with polyclonal rabbit anti-*Ebola* virus serum bound to protein A beads. $^{35}$S-labeled *Ebola* virus structural proteins from virions grown in Vero E6 cells were also immunoprecipitated as a control for each of the virion proteins. Immunoprecipitated proteins were resolved by electrophoresis on an 11% SDS-polyacrylamide gel and were visualized by autoradiography.

Vaccination of Mice with VEE Virus Replicons

Groups of 10 BALB/c or C57BL/6 mice per experiment were subcutaneously injected at the base of the neck with $2\times10^6$ focus-forming units of VRPs encoding the *Ebola* virus genes. As controls, mice were also injected with either a control VRP encoding the Lassa nucleoprotein (NP) or with PBS. For booster inoculations, animals received identical injections at 1 month intervals. Data are recorded as the combined results of 2 or 3 separate experiments.

*Ebola* Infection of Mice

One month after the final booster inoculation, mice were transferred to a BSL-4 containment area and challenged by intraperitoneal (ip) inoculation of 10 plaque-forming units (pfu) of mouse-adapted *Ebola* virus (approximately 300 times the dose lethal for 50% of adult mice). The mice were observed daily, and morbidity and mortality were recorded. Animals surviving at day 21 post-infection were injected again with the same dose of virus and observed for another 21 days.

In some experiments, 4 or 5 mice from vaccinated and control groups were anesthetized and exsanguinated on day 4 (BALB/c mice) or day 5 (C57BL/6 mice) following the initial viral challenge. The viral titers in individual sera were determined by plaque assay.

Passive Transfer of Immune Sera to Naive Mice.

Donor sera were obtained 28 days after the third inoculation with $2\times10^6$ focus-forming units of VRPs encoding the indicated *Ebola* virus gene, the control Lassa NP gene, or from unvaccinated control mice. One mL of pooled donor sera was administered intraperitoneally (ip) to naive, syngeneic mice 24 h prior to intraperitoneal challenge with 10 pfu of mouse-adapted *Ebola* virus.

Vaccination and Challenge of Guinea Pigs.

EboGPVRP or EboNPVRP ($1\times10^7$ focus-forming units in 0.5 ml PBS) were administered subcutaneously to inbred strain 2 or strain 13 guinea pigs (300-400 g). Groups of five guinea pigs were inoculated on days 0 and 28 at one (strain 2) or two (strain 13) dorsal sites. Strain 13 guinea pigs were also boosted on day 126. One group of Strain 13 guinea pigs was vaccinated with both the GP and NP constructs. Blood samples were obtained after vaccination and after viral challenge. Guinea pigs were challenged on day 56 (strain 2) or day 160 (strain 13) by subcutaneous administration of 1000 $LD_{50}$ ($1\times10^4$ PFU) of guinea pig-adapted *Ebola* virus. Animals were observed daily for 60 days, and morbidity (determined as changes in behavior, appearance, and weight) and survival were recorded. Blood samples were taken on the days indicated after challenge and viremia levels were determined by plaque assay.

Virus Titration and Neutralization Assay.

Viral stocks were serially diluted in growth medium, adsorbed onto confluent Vero E6 cells in 6- or 12-well dishes, incubated for 1 hour at 37° C., and covered with an agarose overlay (Moe, J. et al. (1981) *J. Clin. Microbiol.* 13:791-793). A second overlay containing 5% neutral red solution in PBS or agarose was added 6 days later, and plaques were counted the following day. Pooled pre-challenge serum samples from some of the immunized groups were tested for the presence of Ebola-neutralizing antibodies by plaque reduction neutralization assay. Aliquots of *Ebola* virus in growth medium were mixed with serial dilutions of test serum, or with normal serum, or medium only, incubated at 37° C. for 1 h, and used to infect Vero E6 cells. Plaques were counted 1 week later.

Cytotoxic T Cell Assays.

BALB/c and C57BL/6 mice were inoculated with VRPs encoding *Ebola* virus NP or VP24 or the control Lassa NP protein. Mice were euthanized at various times after the last inoculation and their spleens removed. The spleens were gently ruptured to generate single cell suspensions. Spleen cells ($1\times10^6$/ml) were cultured in vitro for 2 days in the presence of 10-25 □M of peptides synthesized from *Ebola* virus NP or VP24 amino acid sequences, and then for an additional 5 days in the presence of peptide and 10% supernatant from concanavalin A-stimulated syngeneic spleen cells. Synthetic peptides were made from *Ebola* virus amino acid sequences predicted by a computer algorithm (HLA Peptide Binding Predictions, Parker, K. C., et al. (1994) *J. Immunol.* 152:163) to have a likelihood of meeting the MHC class I binding requirements of the BALB/c ($H-2^d$) and C57BL/6 ($H-2^b$) haplotypes. Only 2 of 8 peptides predicted by the algorithm and tested to date have been identified as containing CTL epitopes. After in vitro restimulation, the spleen cells were tested in a standard $^{51}$chromium-release assay well known in the art (see, for example, Hart et al. (1991) *Proc. Natl. Acad. Sci. USA* 88: 9449-9452). Percent specific lysis of peptide-coated, MHC-matched or mismatched target cells was calculated as:

$$\frac{\text{Experimental cpm} - \text{Spontaneous cpm} \times 100}{\text{Maximum cpm} - \text{Spontaneous cpm}}$$

Spontaneous cpm are the number of counts released from target cells incubated in medium. Maximum cpm are obtained by lysing target cells with 1% Triton X-100. Experimental cpm are the counts from wells in which target cells are incubated with varying numbers of effector (CTL) cells. Target cells tested were L5178Y lymphoma or P815 mastocytoma cells (MHC matched to the $H2^d$ BALB/c mice and EL4 lymphoma cells (MHC matched to the $H2^b$ C57BL/6 mice). The effector:target (E:T) ratios tested were 25:1, 12:1, 6:1 and 3:1.

EXAMPLE 1

Survival of Mice Inoculated with VRPs Encoding *Ebola* Proteins

Mice were inoculated two or three times at 1 month intervals with $2\times10^6$ focus-forming units of VRPs encoding individual *Ebola* virus genes, or Lassa virus NP as a control, or with phosphate buffered saline (PBS). Mice were challenged with 10 pfu of mouse-adapted *Ebola* virus one month after the final immunization. The mice were observed daily, and morbidity and mortality data are shown in Table 1A for BALB/c mice and Table 1B for C57BL/6 mice. The viral titers in individual sera of some mice on day 4 (BALB/c mice) or day 5 (C57BL/6 mice) following the initial viral challenge were determined by plaque assay.

TABLE 1

Survival Of Mice Inoculated With VRPs Encoding Ebola Proteins

| VRP | #Injections | S/T[1] (%) | MDD[2] | V/T[3] | Viremia[4] |
|---|---|---|---|---|---|
| A. BALB/c Mice | | | | | |
| EboNP | 3 | 30/30 (100%) | | 5/5 | 5.2 |
| | 2 | 19/20 (95%) | 7 | 5/5 | 4.6 |
| EboGP | 3 | 15/29 (52%) | 8 | 1/5 | 6.6 |
| | 2 | 14/20 (70%) | 7 | 3/5 | 3.1 |
| EboVP24 | 3 | 27/30 (90%) | 8 | 5/5 | 5.2 |
| | 2 | 19/20 (95%) | 6 | 4/4 | 4.8 |

TABLE 1-continued

Survival Of Mice Inoculated With VRPs Encoding Ebola Proteins

| VRP | #Injections | S/T[1] (%) | MDD[2] | V/T[3] | Viremia[4] |
|---|---|---|---|---|---|
| EboVP30 | 3 | 17/20 (85%) | 7 | 5/5 | 6.2 |
| | 2 | 11/20 (55%) | 7 | 5/5 | 6.5 |
| EboVP35 | 3 | 5/19 (26%) | 7 | 5/5 | 6.9 |
| | 2 | 4/20 (20%) | 7 | 5/5 | 6.5 |
| EboVP40 | 3 | 14/20 (70%) | 8 | 5/5 | 4.6 |
| | 2 | 17/20 (85%) | 7 | 5/5 | 5.6 |
| LassaNP | 3 | 0/29 (0%) | 7 | 5/5 | 8.0 |
| | 2 | 0/20 (0%) | 7 | 5/5 | 8.4 |
| none(PBS) | 3 | 1/30 (3%) | 6 | 5/5 | 8.3 |
| | 2 | 0/20 (0%) | 6 | 5/5 | 8.7 |
| B. C57BL/6 Mice | | | | | |
| EboNP | 3 | 15/20 (75%) | 8 | 5/5 | 4.1 |
| | 2 | 8/10 (80%) | 9 | ND[5] | ND |
| EboGP | 3 | 19/20 (95%) | 10 | 0/5 | — |
| | 2 | 10/10 (100%) | — | ND | ND |
| EboVP24 | 3 | 0/20 (0%) | 7 | 5/5 | 8.6 |
| EboVP30 | 3 | 2/20 (10%) | 8 | 5/5 | 7.7 |
| EboVP35 | 3 | 14/20 (70%) | 8 | 5/5 | 4.5 |
| EboVP40 | 3 | 1/20 (5%) | 7 | 4/4 | 7.8 |
| LassaNP | 3 | 1/20 (5%) | 7 | 4/4 | 8.6 |
| | 2 | 0/10 (0%) | 7 | ND | ND |
| none(PBS) | 3 | 3/20 (15%) | 7 | 5/5 | 8.6 |
| | 2 | 0/10 (0%) | 7 | ND | ND |

[1]S/T, Survivors/total challenged.
[2]MDD, Mean day to death
[3]V/T, Number of mice with viremia/total number tested.
[4]Geometric mean of $Log_{10}$ viremia titers in PFU/mL. Standard errors for all groups were 1.5 or less, except for the group of BALB/c mice given 2 inoculations of EboGP, which was 2.2.
[5]ND, not determined.

EXAMPLE 2

VP24-Immunized BALB/c Mice Survive a High-Dose Challenge with *Ebola* Virus

BALB/c mice were inoculated two times with $2\times10^6$ focus-forming units of EboVP24VRP. Mice were challenged with either $1\times10^3$ pfu or $1\times10^5$ pfu of mouse-adapted *Ebola* virus 1 month after the second inoculation. Morbidity and mortality data for these mice are shown in Table 2.

TABLE 2

VP24-Immunized BALB/c Mice Survive A High-Dose Challenge With Ebola virus

| Replicon | Challenge Dose | Survivors/Total |
|---|---|---|
| EboVP24 | $1 \times 10^3$ pfu ($3 \times 10^4$ $LD_{50}$) | 5/5 |
| EboVP24 | $1 \times 10^5$ pfu ($3 \times 10^6$ $LD_{50}$) | 5/5 |
| None | $1 \times 10^3$ pfu ($3 \times 10^4$ $LD_{50}$) | 0/4 |
| None | $1 \times 10^5$ pfu ($3 \times 10^6$ $LD_{50}$) | 0/3 |

EXAMPLE 3

Passive Transfer of Immune Sera Can Protect Naive Mice from a Lethal Challenge of *Ebola* Virus Donor sera were obtained 28 days after the third inoculation with $2\times10^6$ focus-forming units of VRPs encoding the indicated *Ebola* virus gene, the control Lassa NP gene, or from unvaccinated control mice. One mL of pooled donor sera was administered intraperitoneally (ip) to naive, syngeneic mice 24 h prior to intraperitoneal challenge with 10 pfu of mouse-adapted *Ebola* virus.

TABLE 3

Passive Transfer of Immune Sera Can Protect Unvaccinated Mice from a Lethal Challenge of Ebola Virus

| Specificity of Donor Sera | Survivors/Total | Mean Day of Death |
|---|---|---|
| A. BALB/c Mice | | |
| Ebola GP | 15/20 | 8 |
| Ebola NP | 1/20 | 7 |
| Ebola VP24 | 0/20 | 6 |
| Ebola VP30 | 0/20 | 7 |
| Ebola VP35 | ND[1] | ND |
| Ebola VP40 | 0/20 | 6 |
| Lassa NP | 0/20 | 7 |
| Normal mouse sera | 0/20 | 6 |
| B. C57BL/6 Mice | | |
| Ebola GP | 17/20 | 7 |
| Ebola NP | 0/20 | 7 |
| Ebola VP24 | ND | ND |
| Ebola VP30 | ND | ND |
| Ebola VP35 | 0/20 | 7 |
| Ebola VP40 | ND | ND |
| Lassa NP | 0/20 | 7 |
| Normal mouse sera | 0/20 | 7 |

[1]ND, not determined

EXAMPLE 4

Immunogenicity and Efficacy of VRepEboGP and VRepEboNP in Guinea Pigs.

EboGPVRP or EboNPVRP ($1 \times 10^7$ IU in 0.5 ml PBS) were administered subcutaneously to inbred strain 2 or strain 13 guinea pigs (300-400 g). Groups of five guinea pigs were inoculated on days 0 and 28 at one (strain 2) or two (strain 13) dorsal sites. Strain 13 guinea pigs were also boosted on day 126. One group of Strain 13 guinea pigs was vaccinated with both the GP and NP constructs. Blood samples were obtained after vaccination and after viral challenge.

Sera from vaccinated animals were assayed for antibodies to *Ebola* by plaque-reduction neutralization, and ELISA. Vaccination with VRepEboGP or NP induced high titers of antibodies to the *Ebola* proteins (Table 4) in both guinea pig strains. Neutralizing antibody responses were only detected in animals vaccinated with the GP construct (Table 4).

Guinea pigs were challenged on day 56 (strain 2) or day 160 (strain 13) by subcutaneous administration of 1000 $LD_{50}$ ($10^4$ PFU) of guinea pig-adapted *Ebola* virus. Animals were observed daily for 60 days, and morbidity (determined as changes in behavior, appearance, and weight) and survival were recorded. Blood samples were taken on the days indicated after challenge and viremia levels were determined by plaque assay. Strain 13 guinea pigs vaccinated with the GP construct, alone or in combination with NP, survived lethal *Ebola* challenge (Table 4). Likewise, vaccination of strain 2 inbred guinea pigs with the GP construct protected 3/5 animals against death from lethal *Ebola* challenge, and significantly prolonged the mean day of death (MDD) in one of the two animals that died (Table 4). Vaccination with NP alone did not protect either guinea pig strain.

TABLE 4

Immunogenicity and efficacy of VRepEboGP and VRepEboNP in guinea pigs

| VRP | ELISA[a] | PRNT$_{50}$ | Survivors/total(MDD[b]) | Viremia[c] d7 | d14 |
|---|---|---|---|---|---|
| A. Strain 2 guinea pigs | | | | | |
| GP | 4.1 | 30 | 3/5 (13 + 2.8) | 2.3 | 1.8 |
| NP | 3.9 | <10 | 0/5 (9.2 + 1.1) | 3.0 | — |
| Mock | <1.5 | <10 | 0/5 (8.8 + 0.5) | 3.9 | — |
| B. Strain 13 guinea pigs | | | | | |
| GP | 4.0 | 140 | 5/5 | <2.0 | <2.0 |
| GP/NP | 3.8 | 70 | 5/5 | <2.0 | <2.0 |
| NP | 2.8 | <10 | 1/5 (8.3 + 2.2) | 4.6 | — |
| Lassa NP | <1.5 | <10 | 2/5 (8.3 + 0.6) | 4.8 | — |

[a]Data are expressed as geometric mean titers, $\log_{10}$.
[b]MDD, mean day to death
[c]Geometric mean of $\log_{10}$ viremia titers in PFU/mL. Standard errors for all groups were 0.9 or less.

EXAMPLE 5

Induction of Murine CTL Responses to *Ebola* Virus NP and *Ebola* Virus VP24 Proteins BALB/c and C57BL/6 mice were inoculated with VRPs encoding *Ebola* virus NP or VP24. Mice were euthanized at various times after the last inoculation and their spleens removed. Spleen cells ($1 \times 10^6$/ml) were cultured in vitro for 2 days in the presence of 10 to 25 $\mu$M of peptides, and then for an additional 5 days in the presence of peptide and 10% supernatant from concanavalin A-stimulated syngeneic spleen cells. After in vitro restimulation, the spleen cells were tested in a standard $^{51}$chromium-release assay. Percent specific lysis of peptide-coated, MHC-matched or mismatched target cells was calculated as:

$$\frac{\text{Experimental cpm} - \text{Spontaneous cpm} \times 100}{\text{Maximum cpm} - \text{Spontaneous cpm}}$$

In the experiments shown, spontaneous release did not exceed 15%.

TABLE 5

Induction of murine CTL responses to Ebola virus NP and Ebola virus VP24 proteins.

| Mice, VRP[1] | Peptide[2] | Cell[3] | % Specific Lysis E:T ratio 25 |
|---|---|---|---|
| BALB/c, VP24 | None | P815 | 55 |
| BALB/c, VP24 | SEQ ID NO: 25 | P815 | 93 |
| C57BL/6, EboNP | None | EL4 | 2 |
| C57BL/6, EboNP[4] | SEQ ID NO: 24 | EL4 | 70 |
| C57BL/6, EboNP | LassaNP | EL4 | 2 |
| C57BL/6, LassaNP | None | L5178Y | 1 |
| C57BL/6, LassaNP | SEQ ID NO: 24 | L5178Y | 0 |
| C57BL/6, LassaNP | None | EL4 | 2 |
| C57BL/6, LassaNP | SEQ ID NO: 24 | EL4 | 6 |

[1]Indicates the mouse strain used and the VRP used as the in vivo immunogen. In vitro restimulation was performed using SEQ ID NO: 24 peptide for BALB/c mice and SEQ ID NO: 23 for all C57BL/6 mice shown.
[2]Indicates the peptide used to coat the target cells for the chromium release assay.
[3]Target cells are MHC-matched to the effector cells, except for the L5178Y cells that are C57BL/6 mismatched.
[4]High levels of specific lysis (>40%) were also observed using E:T ratios of 12, 6, 3, or 1:1.

EXAMPLE 6

Induction of Murine T Cell Responses that Protect Against *Ebola* Challenge

Mice and injections. BALB/c and C57Bl/6 mice were injected sc with $2\times10^6$ IU of VEE virus replicons encoding either the individual *Ebola* genes or Lassa NP (3 injections 1 month apart). The genes used to make replicons are from the human Zaire76 virus. One month after the final immunization, mice were transferred to BSL-4 containment and challenged by ip inoculation of 10 or 1000 pfu (300 or 30000 $LD_{50}$) of mouse-adapted *Ebola* Zaire. This virus has amino acid changes in NP at nt 683 (S to G), VP35 at nt 3163 (A to V), VP24 at nt 10493 (T to I), and in L at nt 14380 (F to L) and nt 16174 (I to V). There are three other nt changes, including an insertion in the intergenic region at nt 10343. GenBank accession number AF499101.

T cell assays. Single cell suspensions were prepared from spleens by passage through cell 70 μM strainers. Spleen cells were depleted of erythrocytes by treatment with buffered ammonium chloride solution and enumerated by trypan blue exclusion on a hemacytometer. For in vitro restimulations, 1-5 μg peptide(s) and human recombinant IL-2 (10 U/ml, National Cancer Institute) were added to a cell density of $1\times10^6$/ml and the cultures incubated 4-7 days. For intracellular IFN-γ staining, splenocytes were cultured at 37° C. for 5 hr with 1-5 μg of peptide(s) or PMA (25 ng/ml) and ionomycin (1.25 ug/ml) in 100 μl complete medium containing 10 μg/ml brefeldin A (BFA). After culture, the cells were blocked with mAbs to FcRIII/II receptor and stained with αCD44 FITC and anti-CD8 Cychrome (Pharmingen, San Diego, Calif.) in PBS/BFA. The cells were then fixed in 1% formaldehyde (Ted Pella, Redding, Calif.), permeabilized with PBS containing 0.5% saponin, and stained with αIFN-γ PE (Pharmingen, San Diego, Calif.). The data were acquired using a FACSCalibur flow cytometer and analyzed with CELLQuest software (Becton-Dickinson. Cytotoxicity assays were performed using target cells (EL4, L5178Y) labeled with $^{51}$Cr ($Na_2CrO_4$; New England Nuclear, Boston, Mass.) and pulsed with peptide for 1.5 hours. Unpulsed target cells were used as negative controls. Various numbers of effector cells were incubated with 2500 target cells for 4 hours. Percentage specific release was calculated as: % specific release=(experimental−spontaneous)/(maximum−spontaneous)×100. Spontaneous release values were obtained by incubation of target cells in medium alone and were routinely <10% of maximum release. Maximum release values were obtained by the addition of 100 μl 1% TritonX-100.

Adoptive transfer experiments. After in vitro restimulation, cells are Ficoll purified, washed three times with 0.3M methyl-a-D-mannopyranoside and twice with complete media. Cells are counted and adjusted to $25.0\times10^6$ cells/ml in endotoxin-free PBS. A total volume of 0.2 mls is given to each mouse by i.p. injection 4 hr before challenge with 1000 PFU of mouse-adapted *Ebola* virus. Animals are observed and sickness or death is noted on daily charts.

As shown in Table A, this data identifies the protective mechanism induced by VRP vaccination, showing the role of T cells. It indicates the ability to predict protection from in vitro assays, specifically the intracellular cytokine and chromium release assays. Thus, a positive ICC result is reasonably predictive of conferred protection, even if the protection is listed as incomplete; the rest of the data strongly indicate protection. Notably, where the CTL sequences are conserved between Zaire and the other *Ebola* viruses, cross-protection may reasonably be inferred. (The protection in Table A refers to adoptive transfer of CTLs to unvaccinated mice before challenge, not the vaccination with a certain protein.)

EXAMPLE 7

Determination of Interference in Protection by Multiple Replicons

The purpose of this experiment was to determine if multiple VEE replicons that do not provide complete protection (VP24, 30, 40 in BL/6 mice) will interfere with a protective replicon *Ebola* NP that has defined CTL epitopes. Co-administration did not interfere with the induction of protection.

| Vaccine | Survival |
| --- | --- |
| VRep EBOV NP, VP24, VP30, VP40 | 10/10 |
| VRep EBOV NP | 6/6 |
| PBS | 0/7 |

The CTLs to NP are CD8(+), and recognize epitopes SEQ ID NO:24, 26 and 27. Evaluation of the ability to lyse peptide-pulsed target cells was assessed using spleen cells from mice vaccinated with the EBOC VRepNP alone, or all four replicons (NP, VP24, VP30 and VP40). Although responses were somewhat lower in the mice receiving four replicons, the threshold of immunity was maintained.

| Vaccine | Effector/target ratio | % Lysis of target cells coated with peptide (background on untreated target cells is subtracted) | | |
| --- | --- | --- | --- | --- |
| | | NP-1 | NP-8 | NP-17 |
| NP | 100:1 | 55 | 31 | 64 |
| | 50:1 | 61 | 23 | 45 |
| | 25:1 | 67 | 15 | 31 |
| | 12:1 | 51 | 13 | 21 |
| Mix | 100:1 | 41 | 40 | 45 |
| | 50:1 | 37 | 32 | 28 |
| | 25:1 | 26 | 33 | 19 |
| | 12:1 | 19 | 18 | 12 |

EXAMPLE 8

Improved Efficacy Induced by a Cocktail Formulation of Suboptimal EBOV Vrep

In studies where we examined the protective efficacy of replicons individually, we observed that some replicons (such as VP30, VP24 and VP40) protected fewer than 100% of the mice. When protection was less than 50%, we suggested that the protein was not particularly protective for that mouse strain. However, in some cases, we did observe that 20-30% of the mice survived, suggesting that we might be able to optimize our vaccine strategy to provide protection with those proteins. As we are evaluating a cocktail formulation, we approached this issue by injecting mice with combinations of the three VP replicons than had poor efficacy in C57Bl/6 mice.

C57BL/6 mice were injected SC at the base of the neck with $2.0\times10^6$ packaged VEE virus replicon particles for each Ebola VP protein, then rested for 27 days and then boosted twice at days 28 and 56. On day 84, mice were injected intraperitoneally with approximately 3×10⁴ LD50 (1000 PFU) of mouse-adapted *Ebola* virus.

| Strain  | Vaccine                      | Survival |
|---------|------------------------------|----------|
| C57BL/6 | VRep VP35                    | 30/30    |
| C57BL/6 | VReps VP35, VP30, VP24, VP40 | 30/30    |
| C57BL/6 | Medium                       | 0/23     |
| C57BL/6 | VReps VP30, VP24, VP40       | 28/30    |

The data indicate that combining the three VP replicons provided significantly better protection than when we administered them singly. Of note, the VP24 replicon has never protected a single C57BL/6 mouse when administered alone and is not likely contributing to protection. However, importantly, its inclusion in the formulation also does not interfere with induction of protective responses to the other VPs.

These data shows that a cocktail formulation may be a preferred vaccine because it induces a broader array of T cells (i.e. CTLs to multiple proteins) and that, together, these may meet the threshold needed for protection. We expect the same phenomenon will apply to non-human primate studies. This also provides support for the inclusion of multiple Ebola peptides/proteins in a cocktail formulation. As an example, if a human infected with Ebola needs 1 million effectors, but vaccination induces only 400,000 to each protein, it may be additive to have 1.2 million spread across 3 proteins. Otherwise, waiting one day for that person's cells to divide to 800,000 and a second day to cross 1 million— but that would likely be too late for survival.

Figure 2A:
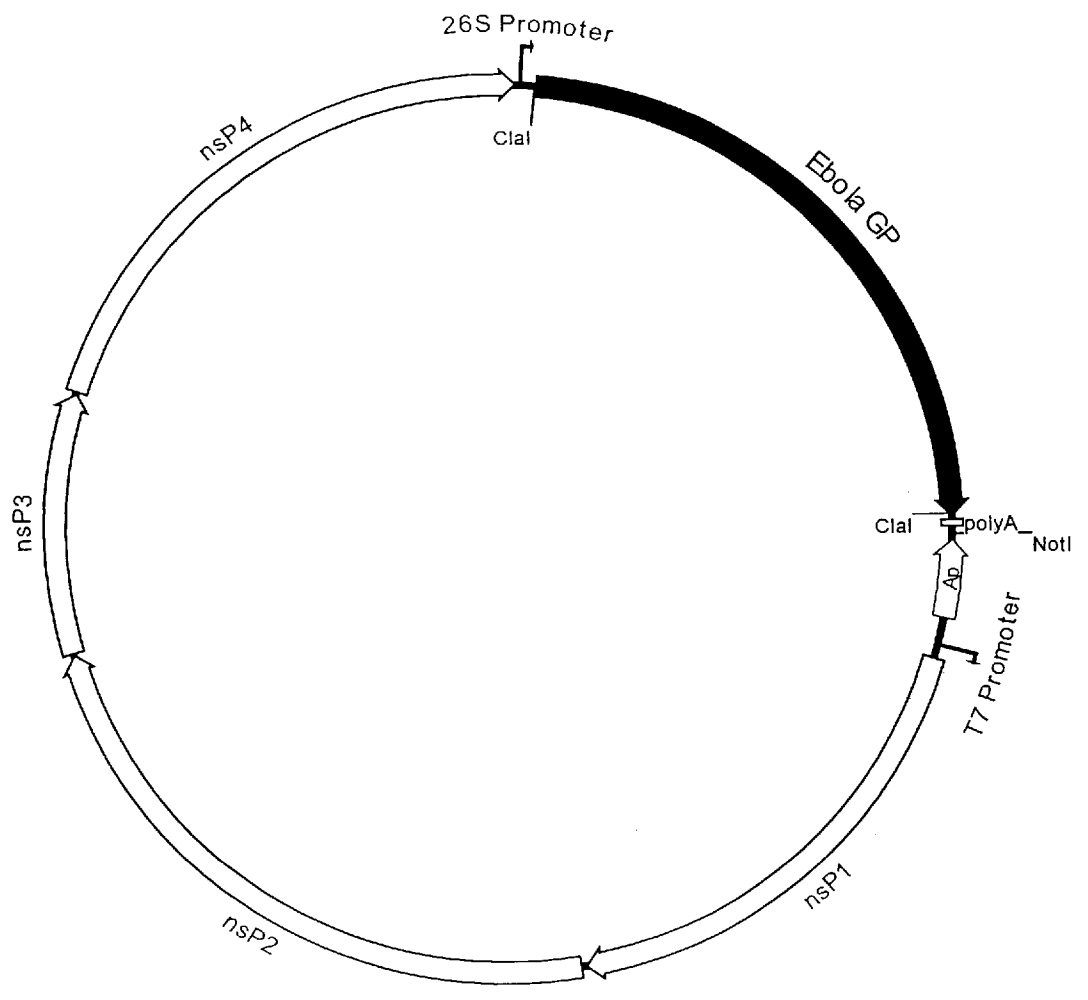
Figure 2B:
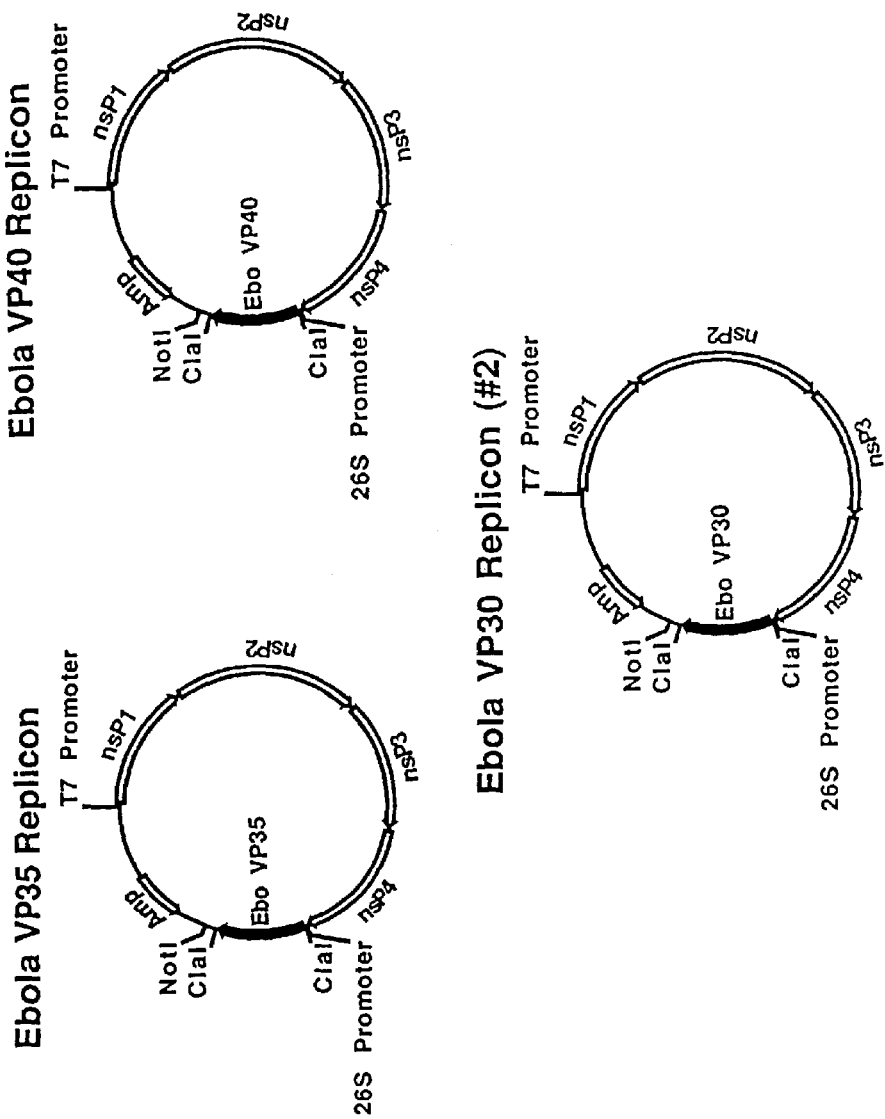
Figure 2C:
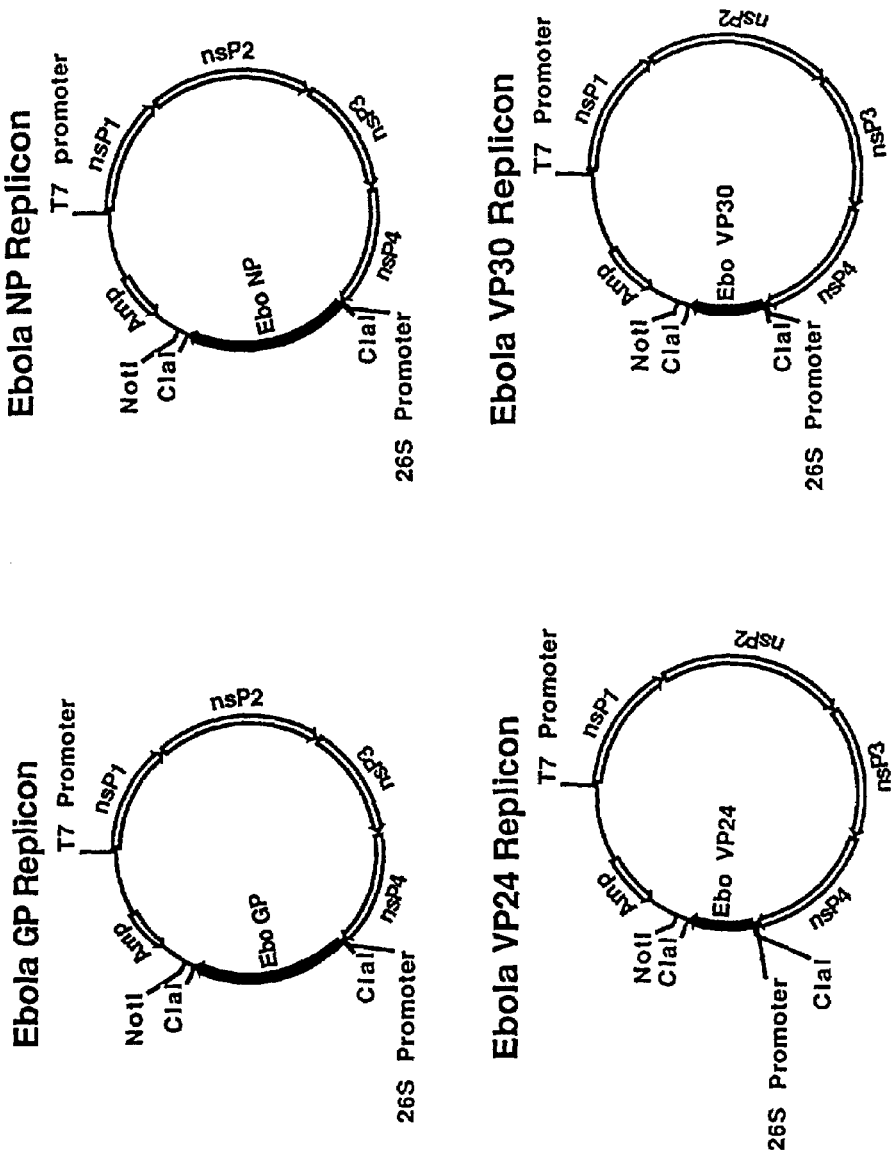
Figure 4:
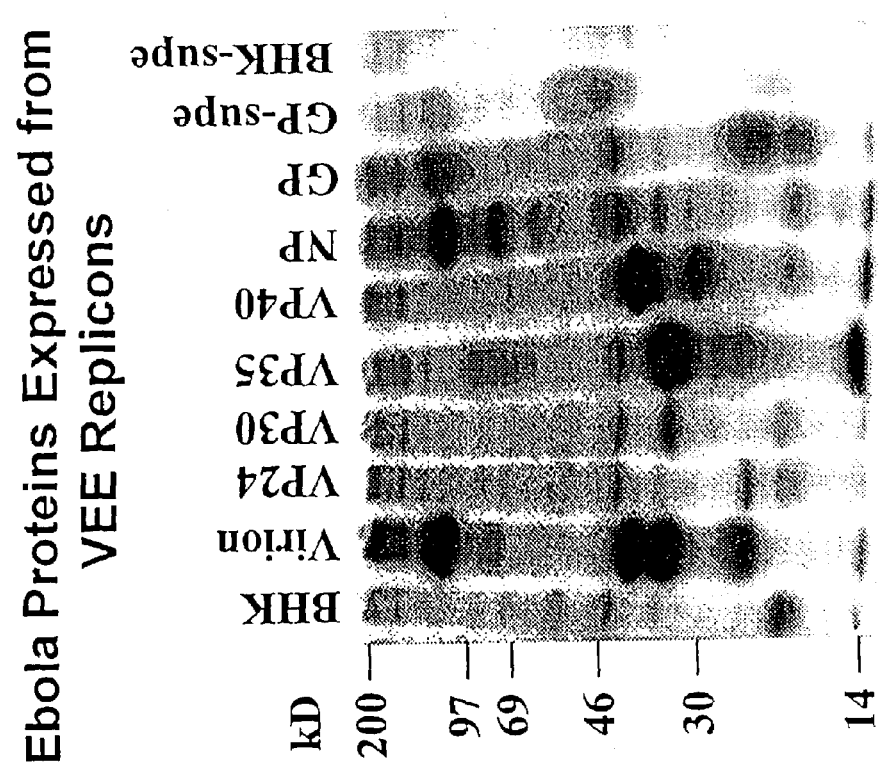

*Ebola Zaire* 1976 (Mayinga) virus causes acute hemorrhagic fever characterized by high mortality. There are no current vaccines or effective therapeutic measures to protect individuals who are exposed to this virus. In addition, it is not known which genes are essential for evoking protective immunity and should therefore be included in a vaccine designed for human use. In this study, the GP, NP, VP24, VP30, VP35, and VP40 virion protein genes of the *Ebola Zaire* 1976 (Mayinga) virus were cloned and inserted into a Venezuelan equine encephalitis (VEE) virus replicon vector (VRep) as shown in FIGS. 2A and 2B. These VReps were packaged as VEE replicon particles (VRPs) using the VEE virus structural proteins provided as helper RNAs, as shown in FIG. 3. This enables expression of the *Ebola* virus proteins in host cells. The *Ebola* virus proteins produced from these constructs were characterized in vitro and were shown to react with polyclonal rabbit anti-*Ebola* virus antibodies bound to Protein A beads following SDS gel electrophoresis of immunoprecipitated proteins (FIG. 4).

The *Ebola* virus genes were sequenced from the VEE replicon clones and are listed here as SEQ ID NO:1 (GP), 2 (NP), 3 (VP24), 4 (VP30), 5 (VP35), 6 (VP40), and 7 (VP30#2) as described below. The corresponding amino acid sequences of the *Ebola* proteins expressed from these replicons are listed as SEQ ID NO: 17, 18, 19, 20, 21, 22, and 23, respectively. Changes in the DNA sequence relative to the sequence published by Sanchez et al. (1993) are described relative to the nucleotide (nt) sequence number from GenBank (accession number L11365).

The sequence we obtained for *Ebola* virus GP (SEQ ID NO:1) differed from the GenBank sequence by a transition from A to G at nt 8023. This resulted in a change in the amino acid sequence from Ile to Val at position 662 (SEQ ID NO: 17).

The DNA sequence we obtained for *Ebola* virus NP (SEQ ID NO:2) differed from the GenBank sequence at the following 4 positions: insertion of a C residue between nt 973 and 974, deletion of a G residue at nt 979, transition from C to T at nt 1307, and a transversion from A to C at nt 2745. These changes resulted in a change in the protein sequence from Arg to Glu at position 170 and a change from Leu to Phe at position 280 (SEQ ID NO: 18).

The *Ebola* virus VP24 (SEQ ID NO:3) gene differed from the GenBank sequence at 6 positions, resulting in 3 non-conservative changes in the amino acid sequence. The changes in the DNA sequence of VP24 consisted of a transversion from G to C at nt 10795, a transversion from C to G at nt 10796, a transversion from T to A at nt 10846, a transversion from A to T at nt 10847, a transversion from C to G at nt 11040, and a transversion from C to G at nt 11041. The changes in the amino acid sequence of VP24 consisted of a Cys to Ser change at position 151, a Leu to His change at position 168, and a Pro to Gly change at position 233 (SEQ ID NO: 19).

We have included 2 different sequences for the *Ebola* virus VP30 gene (SEQ ID NOS:4 and SEQ ID NO:7). Both of these sequences differ from the GenBank sequence by the insertion of an A residue in the upstream noncoding sequence between nt 8469 and 8470 and an insertion of a T residue between nt 9275 and 9276 that results in a change in the open reading frame of VP30 and VP30#2 after position 255 (SEQ ID NOS:20 and SEQ ID NO:23). As a result, the C-terminus of the VP30 protein differs significantly from that previously reported. In addition to these 2 changes, the VP30#2 gene in SEQ ID NO:23 contains a conservative transition from T to C at nt 9217. Because the primers originally used to clone the VP30 gene into the replicon were designed based on the GenBank sequence, the first clone that we constructed (SEQ ID NO:4) did not contain what we believe to be the authentic C-terminus of the protein. Therefore, in the absence of the VP30 stop codon, the C-terminal codon was replaced with 37 amino acids derived from the vector sequence. The resulting VP30 construct therefore differed from the GenBank sequence in that it contained 32 amino acids of VP30 sequence (positions 256 to 287, SEQ ID NO:20) and 37 amino acids of irrelevant sequence (positions 288 to 324, SEQ ID NO:20) in the place of the C-terminal 5 amino acids reported in GenBank. However, inclusion of 37 amino acids of vector sequence in place of the C-terminal amino acid (Pro, SEQ ID NO:23) did not inhibit the ability of the protein to serve as a protective antigen in BALB/c mice. We have also determined that a VEE replicon construct (SEQ ID NO:7), which contains the authentic C-terminus of VP30 (VP30#2, SEQ ID NO:23), is able to protect mice against a lethal *Ebola* challenge.

The DNA sequence for *Ebola* virus VP35 (SEQ ID NO:5) differed from the GenBank sequence by a transition from T to C at nt 4006, a transition from T to C at nt 4025, and an insertion of a T residue between nt 4102 and 4103. These sequence changes resulted in a change from a Ser to a Pro at position 293 and a change from Phe to Ser at position 299 (SEQ ID NO:21). The insertion of the T residue resulted in a change in the open reading frame of VP35 from that previously reported by Sanchez et al. (1993) following amino acid number 324. As a result, *Ebola* virus VP35 encodes for a protein of 340 amino acids, where amino acids 325 to 340 (SEQ ID NO:21) differ from and replace the C-terminal 27 amino acids of the previously published sequence.

Sequencing of VP30 and VP35 was also performed on RT/PCR products from RNA derived from cells that were infected with *Ebola* virus 1976, *Ebola* virus 1995 or the mouse-adapted *Ebola* virus. The changes noted above for the VRep constructs were also found in these *Ebola* viruses. Thus, we believe that these changes are real events and not artifacts of cloning.

The *Ebola* virus VP40 differed from the GenBank sequence by a transversion from a C to G at nt 4451 and a transition from a G to A at nt 5081. These sequence changes did not alter the protein sequence of VP40 (SEQ ID NO:22) from that of the published sequence.

To evaluate the protective efficacy of individual *Ebola* virus proteins and to determine whether the major histocompatibility (MHC) genes influence the immune response to *Ebola* virus antigens, two MHC-incompatible strains of mice were vaccinated with VRPs expressing an *Ebola* protein. As controls for these experiments, some mice were injected with VRPs expressing the nucleoprotein of Lassa virus or were injected with phosphate-buffered saline (PBS). Following *Ebola* virus challenge, the mice were monitored for morbidity and mortality, and the results are shown in Table 1.

The GP, NP, VP24, VP30, and VP40 proteins of *Ebola* virus generated either full or partial protection in BALB/c mice, and may therefore be useful components of a vaccine for humans or other mammals. Vaccination with VRPs encoding the NP protein afforded the best protection. In this case, 100% of the mice were protected after three inoculations and 95% of the mice were protected after two inoculations. The VRP encoding VP24 also protected 90% to 95% of BALB/c mice against *Ebola* virus challenge. In separate experiments (Table 2), two or three inoculations with VRPs encoding the VP24 protein protected BALB/c mice from a high dose ($1 \times 10^5$ plaque—forming units ($3 \times 10^6$ LD50)) of mouse-adapted *Ebola* virus.

Example 1 shows that vaccination with VRPs encoding GP protected 52-70% of BALB/c mice. The lack of protection was not due to a failure to respond to the VRP encoding GP, as all mice had detectable *Ebola* virus-specific serum antibodies after vaccination. Improved results were later seen, which are thought to be dose-dependent. Further, as shown in Examples 6-8, combining suboptimal formulations gives dramatically better protection.

Also in Example 1, some protective efficacy was further observed in BALB/c mice vaccinated two or three times with VRPs expressing the VP30 protein (55% and 85%, respectively),or the VP40 protein (70% and 80%, respectively). The VP35 protein was not efficacious in the BALB/c mouse model, as only 20% and 26% of the mice were protected after either two or three doses, respectively. Again, improved results were later seen, which are thought to be dose-dependent; and we found that combining suboptimal formulations gives dramatically better protection (e.g., combination of VP24, VP30 and VP40).

Geometric mean titers of viremia were markedly reduced in BALB/c mice vaccinated with VRPs encoding *Ebola* virus proteins after challenge with *Ebola* virus, indicating an ability of the induced immune responses to reduce virus replication (Table 1A). In this study, immune responses to the GP protein were able to clear the virus to undetectable levels within 4 days after challenge in some mice.

When the same replicons were examined for their ability to protect C57BL/6 mice from a lethal challenge of *Ebola* virus, only the GP, NP, and VP35 proteins were efficacious (Table 1B). The best protection, 95% to 100%, was observed in C57BL/6 mice inoculated with VRPs encoding the GP protein. Vaccination with VRPs expressing NP protected 75% to 80% of the mice from lethal disease. In contrast to what was observed in the BALB/c mice, the VP35 protein was the only VP protein able to significantly protect the C57BL/6 mice. In this case, 3 inoculations with VRPs encoding VP35 protected 70% of the mice from *Ebola* virus challenge. The reason behind the differences in protection in the two mouse strains is believed to be due to the ability of the immunogens to sufficiently stimulate the cellular immune system. As with the BALB/c mice, the effects of the induced immune responses were also observed in reduced viremias and, occasionally, in a prolonged time to death of C57BL/6 mice.

Example 4 shows that VRPs expressing *Ebola* virus GP or NP were also evaluated for protective efficacy in a guinea pig model. Sera from vaccinated animals were assayed for antibodies to *Ebola* by western blotting, IFA, plaque-reduction neutralization, and ELISA. Vaccination with either VRP (GP or NP) induced high titers of antibodies to the *Ebola* proteins (Table 4) in both guinea pig strains. We later found that VP40 induced high titers (4 logs) in mice. Neutralizing antibody responses were only detected in animals vaccinated with the VRP expressing GP (Table 4).

As shown in Example 4, vaccination of strain 2 inbred guinea pigs with the GP construct protected 3/5 animals against death from lethal *Ebola* challenge, and significantly prolonged the mean day of death in one of the two animals that died (Table 4). All of the strain 13 guinea pigs vaccinated with the GP construct, alone or in combination with NP, survived lethal *Ebola* challenge (Table 4). Vaccination with NP alone did not protect either guinea pig strain from challenge with the guinea pig-adapted *Ebola* virus. Of note, guinea pigs are also inbred, and the failure of NP to protect may indicate that they could not respond with appropriate T cells, but could make protective antibodies to GP. This is further support for our preferred embodiments including multiple peptides and proteins, and even all six of the *Ebola* proteins.

As shown in Example 3, to identify the immune mechanisms that mediate protection against *Ebola* virus and to determine whether antibodies are sufficient to protect against lethal disease, passive transfer studies were performed. One mL of immune sera, obtained from mice previously vaccinated with one of the *Ebola* virus VRPs, was passively administered to unvaccinated mice 24 hours before challenge with a lethal dose of mouse-adapted *Ebola* virus. Antibodies to GP, but not to NP or the VP proteins, protected mice from an *Ebola* virus challenge (Table 3). Antibodies to GP protected 75% of the BALB/c mice and 85% of the C57BL/6 mice from death. When the donor sera were examined for their ability to neutralize *Ebola* virus in a plaque-reduction neutralization assay, a 1:20 to 1:40 dilution of the GP-specific antisera reduced the number of viral plaque-forming units by at least 50% (data not shown). In contrast, antisera to the NP and VP proteins did not neutralize *Ebola* virus at a 1:20 or 1:40 dilution. These results are consistent with the finding that GP is the only viral protein found on the surface of Ebola virus, and is likely to induce virus-neutralizing antibodies.

As shown in Examples 5 and 6, cince the NP and VP proteins of *Ebola* virus are internal virion proteins to which antibodies are not sufficient for protection, it is likely that cytotoxic T lymphocytes (CTLs) are also important for protection against *Ebola* virus. The inventors investigated cellular immune responses to individual *Ebola* virus proteins expressed from VRPs identified CTL responses to the VP24 and NP proteins (Table 5). One CTL epitope that we identified for the *Ebola* virus NP is recognized by C57BL/6 ($H-2^b$) mice, and has an amino acid sequence of, or contained within, the following 11 amino acids: VYQVNN-LEEIC (SEQ ID NO:24). Vaccination with EboNPVRP and in vitro restimulation of spleen cells with this peptide consistently induces strong CTL responses in C57BL/6 (H-$2^b$) mice. In vivo vaccination to *Ebola* virus NP is required to detect the CTL activity, as evidenced by the failure of cells from C57BL/6 mice vaccinated with Lassa NP to develop lytic activity to peptide (SEQ ID NO:24) after in vitro restimulation with it. Specific lysis has been observed using very low effector:target ratios (<2:1). This CTL epitope is H-$2^b$ restricted in that it is not recognized by BALB/c (H-$2^d$) cells treated the same way (data not shown), and H-$2^b$ effector cells will not lyse MHC-mismatched target cells coated with this peptide.

A CTL epitope in the VP24 protein was also identified. It is recognized by BALB/c (H-$2^d$) mice, and has an amino acid sequence of, or contained within, the following 23 amino acids: LKFINKLDALLVVNYNGLLSSIF (SEQ ID NO:25). In the data shown in Table 5, high (>90%) specific lysis of P815 target cells coated with this peptide was observed. The background lysis of cells that were not peptide-coated was also high (>50%), which is probably due to the activity of natural killer cells. We are planning to repeat this experiment using the L5178Y target cells, which are not susceptible to natural killer cells. This shows that CTLs mediated protection, which is further demonstrated by the evidence in Examples 6, 7 and 8.

What is claimed is:

1. An isolated glycoprotein (GP) *Ebola* peptide comprising the sequence specified in SEQ ID NO:29, or consisting of an isolated peptide fragment of SEQ ID NO:29 comprising at least 9 consecutive amino acids which includes the amino acid threonine corresponding to position 14 in SEQ ID NO:29.

2. An isolated peptide fragment consisting of YFG-PAAEGI (SEQ ID NO:42).

3. A composition comprising the isolated peptide of SEQ ID NO: 29 or an isolated peptide consisting of SEQ ID NO:42, in an effective immunogenic amount in a pharmaceutically acceptable carrier and/or adjuvant.

4. An immunogenic composition comprising the isolated peptide of SEQ ID NO: 29 or an isolated peptide consisting of SEQ ID NO:42, in an effective immunogenic amount in a pharmaceutically acceptable carrier and/or adjuvant.

5. A composition comprising recombinant virus replicon particles expressing the peptide of SEQ ID NO:29 or an isolated peptide consisting of SEQ ID NO: 42, in an effective immunogenic amount in a pharmaceutically acceptable carrier and/or adjuvant.

6. The composition of claim 5, wherein the recombinant virus replicon particles are produced from a replicon vector selected from the group consisting of Venezuelan Equine Encephalitis (VEE) virus, eastern equine encephalitis, western equine encephalitis, Semliki forest and Sindbis.

* * * * *

SEQUENCE LISTING

```
<160> NUMBER OF SEQ ID NOS: 53

<210> SEQ ID NO 1
<211> LENGTH: 2298
<212> TYPE: DNA
<213> ORGANISM: Ebola zaire

<400> SEQUENCE: 1
atcgataagc tcggaattcg agctcgcccg gggatcctct agagtcgaca acaacacaat      60
gggcgttaca ggaatattgc agttacctcg tgatcgattc aagaggacat cattctttct     120
ttgggtaatt atccttttcc aaagaacatt ttccatccca cttggagtca tccacaatag     180
cacattacag gttagtgatg tcgacaaact agtttgtcgt gacaaactgt catccacaaa     240
tcaattgaga tcagttggac tgaatctcga agggaatgga gtggcaactg acgtgccatc     300
tgcaactaaa agatggggct tcaggtccgg tgtcccacca aaggtggtca attatgaagc     360
tggtgaatgg gctgaaaact gctacaatct tgaaatcaaa aaacctgacg ggagtgagtg     420
tctaccagca gcgccagacg ggattcgggg cttcccccgg tgccggtatg tgcacaaagt     480
atcaggaacg ggaccgtgtg ccggagactt tgccttccat aaagagggtg ctttcttcct     540
gtatgatcga cttgcttcca cagttatcta ccgaggaacg actttcgctg aaggtgtcgt     600
tgcatttctg atactgcccc aagctaagaa ggacttcttc agctcacacc ccttgagaga     660
gccggtcaat gcaacggagg acccgtctag tggctactat tctaccacaa ttagatatca     720
ggctaccggt tttggaacca atgagacaga gtacttgttc gaggttgaca atttgaccta     780
cgtccaactt gaatcaagat tcacaccaca gtttctgctc cagctgaatg agacaatata     840
tacaagtggg aaaaggagca ataccacggg aaaactaatt tggaaggtca accccgaaat     900
tgatacaaca atcgggagt gggccttctg ggaaactaaa aaaaacctca ctagaaaat       960 tcgcagtgaa gagttgtctt tcacagttgt atcaacgga gccaaaaaca tcagtggtca    1020
gagtccggcg cgaacttctt ccgacccagg gaccaacaca caactgaag accacaaaat     1080 catggcttca gaaaattcct ctgcaatggt tcaagtgcac agtcaaggaa gggaagctgc    1140
agtgtcgcat ctaacaaccc ttgccacaat ctccacgagt ccccaatccc tcacaaccaa    1200
accaggtccg gacaacagca cccataatac acccgtgtat aaacttgaca tctctgaggc    1260
aactcaagtt gaacaagatc accgcagaac agacaacgac agcacagcct ccgacactcc    1320
ctctgccacg accgcagccg gaccccaaa agcagagaac accaacacga gcaagagcac    1380
tgacttcctg gaccccgcca ccacaacaag tcccaaaaac cacagcgaga ccgctggcaa    1440
```

-continued

```
caacaacact catcaccaag ataccggaga agagagtgcc agcagcggga agctaggctt    1500
aattaccaat actattgctg gagtcgcagg actgatcaca ggcgggagaa gaactcgaag    1560
agaagcaatt gtcaatgctc aacccaaatg caaccctaat ttacattact ggactactca    1620
ggatgaaggt gctgcaatcg gactggcctg gataccatat ttcgggccag cagccgaggg    1680
aatttacata gagggctaa tgcacaatca agatggttta atctgtgggt tgagacagct    1740
ggccaacgag acgactcaag ctcttcaact gttcctgaga ccacaactg agctacgcac     1800 cttttcaatc ctcaaccgta aggcaattga tttcttgctg cagcgatggg gcggcacatg    1860
ccacattctg ggaccggact gctgtatcga accacatgat tggaccaaga acataacaga    1920
caaaattgat cagattattc atgattttgt tgataaaacc cttccggacc aggggacaa     1980 tgacaattgg tggacaggat ggagacaatg gataccggca gtattggag ttacaggcgt     2040 tgtaattgca gttatcgctt tattctgtat atgcaaattt gtcttttagt ttttcttcag    2100
attgcttcat ggaaaagctc agcctcaaat caatgaaacc aggatttaat tatatggatt    2160
acttgaatct aagattactt gacaaatgat aatataatac actggagctt taaacatagc    2220
caatgtgatt ctaactcctt taaactcaca gttaatcata acaaggtttt gagtcgacct    2280
gcagccaagc ttatcgat                                                  2298

<210> SEQ ID NO 2
<211> LENGTH: 2428
<212> TYPE: DNA
<213> ORGANISM: Ebola zaire

<400> SEQUENCE: 2
atcgataagc ttggctgcag gtcgactcta gaggatccga gtatggattc tcgtcctcag      60
aaaatctgga tggcgccgag tctcactgaa tctgacatgg attaccacaa gatcttgaca     120
gcaggtctgt ccgttcaaca ggggattgtt cggcaaagag tcatcccagt gtatcaagta     180
aacaatcttg aagaaatttg ccaacttatc atacaggcct ttgaagcagg tgttgatttt    240
caagagagtg cggacagttt ccttctgatg ctttgtcttc atcatgcgta ccagggagat    300
tacaaacttt tcttggaaag tggcgcagtc aagtatttgg aagggcacgg gttccgtttt    360
gaagtcaaga agcgtgatgg agtgaagcga cttgaggaat tgctgccagc agtatctagt    420
ggaaaaaaca ttaagagaac acttgctgcc atgccggaag aggagacaac tgaagctaat    480
gccggtcagt ttctctcctt tgcaagtcta ttccttccga aattggtagt aggagaaaag    540
gcttgccttg agaaggttca aaggcaaatt caagtacatg cagagcaagg actgatacaa    600
tatccaacag cttggcaatc agtaggacac atgatggtga tttccgtttt gatgcgaaca    660
aattttctga tcaaatttct cctaatacac aagggatgc acatggttgc cgggcatgat    720
gccaacgatg ctgtgatttc aaattcagtg gctcaagctc gtttttcagg cttattgatt    780
gtcaaaacag tacttgatca tatcctacaa aagacagaac gaggagttcg tctccatcct    840
cttgcaagga ccgccaaggt aaaaaatgag gtgaactcct ttaaggctgc actcagctcc    900
ctggccaagc atggagagta tgctcctttc gcccgacttt tgaacctttc tggagtaaat    960
aatcttgagc atggtctttt ccctcaacta tcggcaattg cactcggagt cgccacagca    1020
cacgggagta ccctcgcagg agtaaatgtt ggagaacagt atcaacaact cagagaggct    1080
gccactgagg ctgagaagca actccaacaa tatgcagagt ctcgcgaact tgaccatctt    1140
ggacttgatg atcaggaaaa gaaaattctt atgaacttcc atcagaaaaa gaacgaaatc    1200
agcttccagc aaacaaacgc tatggtaact ctaagaaaag agcgcctggc caagctgaca    1260
```

-continued

```
gaagctatca ctgctgcgtc actgcccaaa acaagtggac attacgatga tgatgacgac    1320 attcccttc caggacccat caatgatgac gacaatccta gccatcaaga tgatgatccg      1380
actgactcac aggatacgac cattcccgat gtggtggttg atcccgatga tggaagctac    1440
ggcgaatacc agagttactc ggaaaacggc atgaatgcac cagatgactt ggtcctattc    1500
gatctagacg aggacgacga ggacactaag ccagtgccta atagatcgac caagggtgga    1560
caacagaaga acagtcaaaa gggccagcat atagagggca gacagacaca atccaggcca    1620
attcaaaatg tcccaggccc tcacagaaca atccaccacg ccagtgcgcc actcacggac    1680
aatgacagaa gaaatgaacc ctccggctca accagccctc gcatgctgac accaattaac    1740
gaagaggcag acccactgga cgatgccgac gacgagacgt ctagccttcc gcccttggag    1800
tcagatgatg aagagcagga cagggacgga acttccaacc gcacacccac tgtcgcccca    1860
ccggctcccg tatacagaga tcactctgaa aagaaagaac tccgcaagaa cgagcaacaa    1920
gatcaggacc acactcaaga ggccaggaac caggacagtg acaacaccca gtcagaacac    1980
tcttttgagg agatgtatcg ccacattcta agatcacagg ggccatttga tgctgttttg    2040
tattatcata tgatgaagga tgagcctgta gttttcagta ccagtgatgg caaagagtac    2100
acgtatccag actcccttga agaggaatat ccaccatggc tcactgaaaa agaggctatg    2160
aatgaagaga atagatttgt tacattggat ggtcaacaat tttattggcc ggtgatgaat    2220
cacaagaata aattcatggc aatcctgcaa catcatcagt gaatgagcat ggaacaatgg    2280
gatgattcaa ccgacaaata gctaacatta gtagtccag gaacgaaaac aggaagaatt    2340
tttgatgtct aaggtgtgaa ttattatcac aataaaagtg attcttatt ttgaatttgg      2400 gcgagctcga attcccgagc ttatcgat                                        2428
```

<210> SEQ ID NO 3
<211> LENGTH: 847
<212> TYPE: DNA
<213> ORGANISM: Ebola zaire

<400> SEQUENCE: 3

```
atcgatctcc agacaccaag caagacctga gaaaaaacca tggctaaagc tacgggacga      60
tacaatctaa tatcgcccaa aaaggacctg gagaaagggg ttgtcttaag cgacctctgt    120
aacttcttag ttagccaaac tattcagggg tggaaggttt attgggctgg tattgagttt    180
gatgtgactc acaaaggaat ggccctattg catagactga aaactaatga ctttgccccct    240 gcatggtcaa tgacaaggaa tctctttcct catttatttc aaaatccgaa ttccacaatt    300
gaatcaccgc tgtgggcatt gagagtcatc cttgcagcag gatacaggaa ccagctgatt    360
gaccagtctt tgattgaacc cttagcagga gcccttggtc tgatctctga ttggctgcta    420
acaaccaaca ctaaccattt caacatgcga acacaacgtg tcaaggaaca attgagccta    480
aaaatgctgt cgttgattcg atccaatatt ctcaagttta ttaacaaatt ggatgctcta    540
catgtcgtga actacaacgg attgttgagc agtattgaaa ttggaactca aaatcataca    600
atcatcataa ctcgaactaa catgggtttt ctggtggagc tccaagaacc cgacaaatcg    660
gcaatgaacc gcatgaagcc tgggccggcg aaatttccc tccttcatga gtccacactg    720
aaagcattta cacaaggatc ctcgacacga atgcaaagtt tgattcttga atttaatagc    780
tctcttgcta tctaactaag gtagaatact tcatattgag ctaactcata tatgctgact    840
catcgat                                                                847
```

<210> SEQ ID NO 4
<211> LENGTH: 973
<212> TYPE: DNA
<213> ORGANISM: Ebola zaire

<400> SEQUENCE: 4

| | | | | | |
|---|---|---|---|---|---|
| atcgatcaga | tctgcgaacc | ggtagagttt | agttgcaacc | taacacacat | aaagcattgg | 60 |
| tcaaaaagtc | aatagaaatt | taaacagtga | gtggagacaa | cttttaaatg | gaagcttcat | 120 |
| atgagagagg | acgcccacga | gctgccagac | agcattcaag | ggatggacac | gaccaccatg | 180 |
| ttcgagcacg | atcatcatcc | agagagaatt | atcgaggtga | gtaccgtcaa | tcaaggagcg | 240 |
| cctcacaagt | gcgcgttcct | actgtatttc | ataagaagag | agttgaacca | ttaacagttc | 300 |
| ctccagcacc | taaagacata | tgtccgacct | tgaaaaaagg | atttttgtgt | gacagtagtt | 360 |
| tttgcaaaaa | agatcaccag | ttggagagtt | taactgatag | ggaattactc | ctactaatcg | 420 |
| cccgtaagac | ttgtggatca | gtagaacaac | aattaaatat | aactgcaccc | aaggactcgc | 480 |
| gcttagcaaa | tccaacggct | gatgatttcc | agcaagagga | aggtccaaaa | attaccttgt | 540 |
| tgacactgat | caagacggca | gaacactggg | cgagacaaga | catcagaacc | atagaggatt | 600 |
| caaaattaag | agcattgttg | actctatgtg | ctgtgatgac | gaggaaattc | tcaaaatccc | 660 |
| agctgagtct | tttatgtgag | acacacctaa | ggcgcgaggg | gcttgggcaa | gatcaggcag | 720 |
| aacccgttct | cgaagtatat | caacgattac | acagtgataa | aggaggcagt | tttgaagctg | 780 |
| cactatggca | acaatgggac | ctacaatccc | taattatgtt | tatcactgca | ttcttgaata | 840 |
| ttgctctcca | gttaccgtgt | gaaagttctg | ctgtcgttgt | ttcagggtta | agaacattgg | 900 |
| ttcctcaatc | agataatgag | gaagcttcaa | ccaacccggg | gacatgctca | tggtctgatg | 960 |
| agggtacatc | gat | | | | | 973 |

<210> SEQ ID NO 5
<211> LENGTH: 1148
<212> TYPE: DNA
<213> ORGANISM: Ebola zaire

<400> SEQUENCE: 5

| | | | | | |
|---|---|---|---|---|---|
| atcgatagaa | aagctggtct | aacaagatga | caactagaac | aaagggcagg | ggccatactg | 60 |
| cggccacgac | tcaaaacgac | agaatgccag | gccctgagct | ttcgggctgg | atctctgagc | 120 |
| agctaatgac | cggaagaatt | cctgtaagcg | acatcttctg | tgatattgag | aacaatccag | 180 |
| gattatgcta | cgcatcccaa | atgcaacaaa | cgaagccaaa | cccgaagacg | cgcaacagtc | 240 |
| aaacccaaac | ggacccaatt | tgcaatcata | gttttgagga | ggtagtacaa | acattggctt | 300 |
| cattggctac | tgttgtgcaa | caacaaacca | tcgcatcaga | atcattagaa | caacgcatta | 360 |
| cgagtcttga | gaatggtcta | aagccagttt | atgatatggc | aaaaacaatc | tcctcattga | 420 |
| acaggggttg | tgctgagatg | gttgcaaaat | atgatcttct | ggtgatgaca | accggtcggg | 480 |
| caacagcaac | cgctgcggca | actgaggctt | attgggccga | acatggtcaa | ccaccacctg | 540 |
| gaccatcact | ttatgaagaa | agtgcgattc | ggggtaagat | tgaatctaga | gatgagaccg | 600 |
| tccctcaaag | tgttaggag | gcattcaaca | atctaaacag | taccacttca | ctaactgagg | 660 |
| aaaattttgg | gaaacctgac | atttcggcaa | aggatttgag | aaacattatg | tatgatcact | 720 |
| tgcctggttt | tggaactgct | ttccaccaat | tagtacaagt | gatttgtaaa | ttgggaaaag | 780 |
| atagcaactc | attggacatc | attcatgctg | agttccaggc | cagcctggct | gaaggagact | 840 |
| ctcctcaatg | tgccctaatt | caaattacaa | aaagagttcc | aatcttccaa | gatgctgctc | 900 |

```
cacctgtcat ccacatccgc tctcgaggtg acattccccg agcttgccag aaaagcttgc    960
gtccagtccc accatcgccc aagattgatc gaggttgggt atgtgttttt cagcttcaag   1020
atggtaaaac acttggactc aaaatttgag ccaatctccc ttccctccga aagaggcgaa   1080
taatagcaga ggcttcaact gctgaactat agggtacgtt acattaatga tacacttgtg   1140
agatcgat                                                            1148

<210> SEQ ID NO 6
<211> LENGTH: 1123
<212> TYPE: DNA
<213> ORGANISM: Ebola zaire

<400> SEQUENCE: 6
atcgatccta cctcggctga gagagtgttt tttcattaac cttcatcttg taaacgttga     60
gcaaaattgt taaaaatatg aggcgggtta tattgcctac tgctcctcct gaatatatgg    120
aggccatata ccctgtcagg tcaaattcaa caattgctag aggtggcaac agcaatacag    180
gcttcctgac accggagtca gtcaatgggg acactccatc gaatccactc aggccaattg    240
ccgatgacac catcgaccat gccagccaca caccaggcag tgtgtcatca gcattcatcc    300
ttgaagctat ggtgaatgtc atatcgggcc ccaaagtgct aatgaagcaa attccaattt    360
ggcttcctct aggtgtcgct gatcaaaaga cctacagctt tgactcaact acggccgcca    420
tcatgcttgc ttcatacact atcacccatt tcggcaaggc aaccaatcca cttgtcagag    480
tcaatcggct gggtcctgga atcccggatc atccctcag gctcctgcga attggaaacc    540
aggctttcct ccaggagttc gttcttccgc cagtccaact accccagtat tcacctttg     600 atttgacagc actcaaactg atcacccaac cactgcctgc tgcaacatgg accgatgaca    660
ctccaacagg atcaaatgga gcgttgcgtc caggaatttc atttcatcca aaacttcgcc    720
ccattctttt acccaacaaa agtgggaaga aggggaacag tgccgatcta acatctccgg    780
agaaaatcca agcaataatg acttcactcc aggactttaa gatcgttcca attgatccaa    840
ccaaaaatat catgggaatc gaagtgccag aaactctggt ccacaagctg accggtaaga    900
aggtgacttc taaaaatgga caaccaatca tccctgttct tttgccaaag tacattgggt    960
tggacccggt ggctccagga gacctcacca tggtaatcac acaggattgt gacacgtgtc   1020
attctcctgc aagtcttcca gctgtgattg agaagtaatt gcaataattg actcagatcc   1080
agttttatag aatcttctca gggatagtgc ataacatatc gat                     1123

<210> SEQ ID NO 7
<211> LENGTH: 1165
<212> TYPE: DNA
<213> ORGANISM: Ebola zaire

<400> SEQUENCE: 7
atcgatcaga tctgcgaacc ggtagagttt agttgcaacc taacacacat aaagcattgg     60
tcaaaaagtc aatagaaatt taaacagtga gtggagacaa cttttaaatg gaagcttcat    120
atgagagagg acgcccacga gctgccagac agcattcaag ggatggacac gaccaccatg    180
ttcgagcacg atcatcatcc agagagaatt atcgaggtga gtaccgtcaa tcaaggagcg    240
cctcacaagt gcgcgttcct actgtatttc ataagaagag agttgaacca ttaacagttc    300
ctccagcacc taaagacata tgtccgacct tgaaaaaagg atttttgtgt gacagtagtt    360
tttgcaaaaa agatcaccag ttggagagtt taactgatag ggaattactc ctactaatcg    420
```

-continued

```
cccgtaagac ttgtggatca gtagaacaac aattaaatat aactgcaccc aaggactcgc    480
gcttagcaaa tccaacggct gatgatttcc agcaagagga aggtccaaaa attaccttgt    540
tgacactgat caagacggca gaacactggg cgagacaaga catcagaacc atagaggatt    600
caaaattaag agcattgttg actctatgtg ctgtgatgac gaggaaattc tcaaaatccc    660
agctgagtct tttatgtgag acacacctaa ggcgcgaggg gcttgggcaa gatcaggcag    720
aacccgttct cgaagtatat caacgattac acagtgataa aggaggcagt tttgaagctg    780
cactatggca acaatgggac cgacaatccc taatcatgtt tatcactgca ttcttgaata    840
ttgctctcca gttaccgtgt gaaagttctg ctgtcgttgt ttcagggtta agaacattgg    900
ttcctcaatc agataatgag gaagcttcaa ccaacccggg gacatgctca tggtctgatg    960
agggtacccc ttaataaggc tgactaaaac actatataac cttctacttg atcacaatac   1020
tccgtatacc tatcatcata tatttaatca agacgatatc ctttaaaact tattcagtac   1080
tataatcact ctcgtttcaa attaataaga tgtgcatgat tgccctaata tatgaagagg   1140
tatgatacaa ccctaacaga tcgat                                          1165
```

```
<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence:
      Forward primer for VP24

<400> SEQUENCE: 8
gggatcgatc tccagacacc aagcaagacc                                       30

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence:
      Reverse primer for VP24

<400> SEQUENCE: 9
gggatcgatg agtcagcata tatgagttag ctc                                   33

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Forward primer for VP30

<400> SEQUENCE: 10
cccatcgatc agatctgcga accggtagag                                       30

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:
      Reverse primer for VP30

<400> SEQUENCE: 11
cccatcgatg taccctcatc agaccatgag c                                     31
```

```
<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence:
      Forward primer for VP35

<400> SEQUENCE: 12
gggatcgata gaaaagctgg tctaacaaga tga                           33

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence:
      Reverse primer for VP35

<400> SEQUENCE: 13
cccatcgatc tcacaagtgt atcattaatg taacgt                        36

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:
      Forward primer for VP40

<400> SEQUENCE: 14
cccatcgatc ctacctcggc tgagagagtg                               30

<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      Reverse primer for VP40

<400> SEQUENCE: 15
cccatcgata tgttatgcac tatccctgag aag                           33

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:
      Reverse primer for VP30#2

<400> SEQUENCE: 16
cccatcgatc tgttagggtt gtatcatacc                               30

<210> SEQ ID NO 17
<211> LENGTH: 676
<212> TYPE: PRT
<213> ORGANISM: Ebola zaire

<400> SEQUENCE: 17

Met Gly Val Thr Gly Ile Leu Gln Leu Pro Arg Asp Arg Phe Lys Arg
  1               5                  10                  15

Thr Ser Phe Phe Leu Trp Val Ile Ile Leu Phe Gln Arg Thr Phe Ser
                 20                  25                  30

Ile Pro Leu Gly Val Ile His Asn Ser Thr Leu Gln Val Ser Asp Val
```

-continued

```
                35                  40                  45
Asp Lys Leu Val Cys Arg Asp Lys Leu Ser Ser Thr Asn Gln Leu Arg
 50                  55                  60
Ser Val Gly Leu Asn Leu Glu Gly Asn Gly Val Ala Thr Asp Val Pro
 65                  70                  75                  80
Ser Ala Thr Lys Arg Trp Gly Phe Arg Ser Gly Val Pro Pro Lys Val
                 85                  90                  95
Val Asn Tyr Glu Ala Gly Glu Trp Ala Glu Asn Cys Tyr Asn Leu Glu
                100                 105                 110
Ile Lys Lys Pro Asp Gly Ser Glu Cys Leu Pro Ala Ala Pro Asp Gly
                115                 120                 125
Ile Arg Gly Phe Pro Arg Cys Arg Tyr Val His Lys Val Ser Gly Thr
            130                 135                 140
Gly Pro Cys Ala Gly Asp Phe Ala Phe His Lys Glu Gly Ala Phe Phe
145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
                180                 185                 190
Phe Phe Ser Ser His Pro Leu Arg Glu Pro Val Asn Ala Thr Glu Asp
                195                 200                 205
Pro Ser Ser Gly Tyr Tyr Ser Thr Thr Ile Arg Tyr Gln Ala Thr Gly
                210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
                260                 265                 270
Leu Ile Trp Lys Val Asn Pro Glu Ile Asp Thr Thr Ile Gly Glu Trp
                275                 280                 285
Ala Phe Trp Glu Thr Lys Lys Asn Leu Thr Arg Lys Ile Arg Ser Glu
            290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
                340                 345                 350
Val His Ser Gln Gly Arg Glu Ala Ala Val Ser His Leu Thr Thr Leu
            355                 360                 365
Ala Thr Ile Ser Thr Ser Pro Gln Ser Leu Thr Thr Lys Pro Gly Pro
            370                 375                 380
Asp Asn Ser Thr His Asn Thr Pro Val Tyr Lys Leu Asp Ile Ser Glu
385                 390                 395                 400
Ala Thr Gln Val Glu Gln His His Arg Arg Thr Asp Asn Asp Ser Thr
                405                 410                 415
Ala Ser Asp Thr Pro Ser Ala Thr Thr Ala Ala Gly Pro Pro Lys Ala
                420                 425                 430
Glu Asn Thr Asn Thr Ser Lys Ser Thr Asp Phe Leu Asp Pro Ala Thr
            435                 440                 445
Thr Thr Ser Pro Gln Asn His Ser Glu Thr Ala Gly Asn Asn Asn Thr
450                 455                 460
```

```
His His Gln Asp Thr Gly Glu Glu Ser Ala Ser Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
        515                 520                 525

Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
    610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Val Ile Ala Val Ile Ala Leu Phe Cys Ile Cys
            660                 665                 670

Lys Phe Val Phe
        675

<210> SEQ ID NO 18
<211> LENGTH: 739
<212> TYPE: PRT
<213> ORGANISM: Ebola zaire

<400> SEQUENCE: 18

Met Asp Ser Arg Pro Gln Lys Ile Trp Met Ala Pro Ser Leu Thr Glu
1               5                   10                  15

Ser Asp Met Asp Tyr His Lys Ile Leu Thr Ala Gly Leu Ser Val Gln
                20                  25                  30

Gln Gly Ile Val Arg Gln Arg Val Ile Pro Val Tyr Gln Val Asn Asn
            35                  40                  45

Leu Glu Glu Ile Cys Gln Leu Ile Ile Gln Ala Phe Glu Ala Gly Val
        50                  55                  60

Asp Phe Gln Glu Ser Ala Asp Ser Phe Leu Leu Met Leu Cys Leu His
65                  70                  75                  80

His Ala Tyr Gln Gly Asp Tyr Lys Leu Phe Leu Glu Ser Gly Ala Val
                85                  90                  95

Lys Tyr Leu Glu Gly His Gly Phe Arg Phe Glu Val Lys Lys Arg Asp
            100                 105                 110

Gly Val Lys Arg Leu Glu Glu Leu Leu Pro Ala Val Ser Ser Gly Lys
        115                 120                 125

Asn Ile Lys Arg Thr Leu Ala Ala Met Pro Glu Glu Glu Thr Thr Glu
130                 135                 140

Ala Asn Ala Gly Gln Phe Leu Ser Phe Ala Ser Leu Phe Leu Pro Lys
```

-continued

```
            145                 150                 155                 160
Leu Val Val Gly Glu Lys Ala Cys Leu Glu Lys Val Gln Arg Gln Ile
                165                 170                 175
Gln Val His Ala Glu Gln Gly Leu Ile Gln Tyr Pro Thr Ala Trp Gln
                180                 185                 190
Ser Val Gly His Met Met Val Ile Phe Arg Leu Met Arg Thr Asn Phe
                195                 200                 205
Leu Ile Lys Phe Leu Leu Ile His Gln Gly Met His Met Val Ala Gly
            210                 215                 220
His Asp Ala Asn Asp Ala Val Ile Ser Asn Ser Val Ala Gln Ala Arg
225                 230                 235                 240
Phe Ser Gly Leu Leu Ile Val Lys Thr Val Leu Asp His Ile Leu Gln
                245                 250                 255
Lys Thr Glu Arg Gly Val Arg Leu His Pro Leu Ala Arg Thr Ala Lys
                260                 265                 270
Val Lys Asn Glu Val Asn Ser Phe Lys Ala Ala Leu Ser Ser Leu Ala
            275                 280                 285
Lys His Gly Glu Tyr Ala Pro Phe Ala Arg Leu Leu Asn Leu Ser Gly
            290                 295                 300
Val Asn Asn Leu Glu His Gly Leu Phe Pro Gln Leu Ser Ala Ile Ala
305                 310                 315                 320
Leu Gly Val Ala Thr Ala His Gly Ser Thr Leu Ala Gly Val Asn Val
                325                 330                 335
Gly Glu Gln Tyr Gln Gln Leu Arg Glu Ala Ala Thr Glu Ala Glu Lys
            340                 345                 350
Gln Leu Gln Gln Tyr Ala Glu Ser Arg Glu Leu Asp His Leu Gly Leu
            355                 360                 365
Asp Asp Gln Glu Lys Lys Ile Leu Met Asn Phe His Gln Lys Lys Asn
        370                 375                 380
Glu Ile Ser Phe Gln Gln Thr Asn Ala Met Val Thr Leu Arg Lys Glu
385                 390                 395                 400
Arg Leu Ala Lys Leu Thr Glu Ala Ile Thr Ala Ala Ser Leu Pro Lys
                405                 410                 415
Thr Ser Gly His Tyr Asp Asp Asp Asp Ile Pro Phe Pro Gly Pro
                420                 425                 430
Ile Asn Asp Asp Asn Pro Gly His Gln Asp Asp Pro Thr Asp
        435                 440                 445
Ser Gln Asp Thr Thr Ile Pro Asp Val Val Asp Pro Asp Asp Gly
            450                 455                 460
Ser Tyr Gly Glu Tyr Gln Ser Tyr Ser Glu Asn Gly Met Asn Ala Pro
465                 470                 475                 480
Asp Asp Leu Val Leu Phe Asp Leu Asp Glu Asp Asp Glu Asp Thr Lys
                485                 490                 495
Pro Val Pro Asn Arg Ser Thr Lys Gly Gly Gln Lys Asn Ser Gln
            500                 505                 510
Lys Gly Gln His Ile Glu Gly Arg Gln Thr Gln Ser Arg Pro Ile Gln
            515                 520                 525
Asn Val Pro Gly Pro His Arg Thr Ile His His Ala Ser Ala Pro Leu
            530                 535                 540
Thr Asp Asn Asp Arg Arg Asn Glu Pro Ser Gly Ser Thr Ser Pro Arg
545                 550                 555                 560
Met Leu Thr Pro Ile Asn Glu Glu Ala Asp Pro Leu Asp Asp Ala Asp
                565                 570                 575
```

-continued

```
Asp Glu Thr Ser Ser Leu Pro Pro Leu Glu Ser Asp Asp Glu Glu Gln
            580                 585                 590

Asp Arg Asp Gly Thr Ser Asn Arg Thr Pro Thr Val Ala Pro Pro Ala
        595                 600                 605

Pro Val Tyr Arg Asp His Ser Glu Lys Lys Glu Leu Pro Gln Asp Glu
        610                 615                 620

Gln Gln Asp Gln Asp His Thr Gln Glu Ala Arg Asn Gln Asp Ser Asp
625                 630                 635                 640

Asn Thr Gln Ser Glu His Ser Phe Glu Met Tyr Arg His Ile Leu
                645                 650                 655

Arg Ser Gln Gly Pro Phe Asp Ala Val Leu Tyr Tyr His Met Met Lys
                660                 665                 670

Asp Glu Pro Val Val Phe Ser Thr Ser Asp Gly Lys Glu Tyr Thr Tyr
                675                 680                 685

Pro Asp Ser Leu Glu Glu Glu Tyr Pro Pro Trp Leu Thr Glu Lys Glu
        690                 695                 700

Ala Met Asn Glu Glu Asn Arg Phe Val Thr Leu Asp Gly Gln Gln Phe
705                 710                 715                 720

Tyr Trp Pro Val Met Asn His Lys Asn Lys Phe Met Ala Ile Leu Gln
                725                 730                 735

His His Gln
```

<210> SEQ ID NO 19
<211> LENGTH: 251
<212> TYPE: PRT
<213> ORGANISM: Ebola zaire

<400> SEQUENCE: 19

```
Met Ala Lys Ala Thr Gly Arg Tyr Asn Leu Ile Ser Pro Lys Lys Asp
  1               5                  10                  15

Leu Glu Lys Gly Val Val Leu Ser Asp Leu Cys Asn Phe Leu Val Ser
                20                  25                  30

Gln Thr Ile Gln Gly Trp Lys Val Tyr Trp Ala Gly Ile Glu Phe Asp
            35                  40                  45

Val Thr His Lys Gly Met Ala Leu Leu His Arg Leu Lys Thr Asn Asp
        50                  55                  60

Phe Ala Pro Ala Trp Ser Met Thr Arg Asn Leu Phe Pro His Leu Phe
 65                  70                  75                  80

Gln Asn Pro Asn Ser Thr Ile Glu Ser Pro Leu Trp Ala Leu Arg Val
                85                  90                  95

Ile Leu Ala Ala Gly Ile Gln Asp Gln Leu Ile Asp Gln Ser Leu Ile
            100                 105                 110

Glu Pro Leu Ala Gly Ala Leu Gly Leu Ile Ser Asp Trp Leu Leu Thr
        115                 120                 125

Thr Asn Thr Asn His Phe Asn Met Arg Thr Gln Arg Val Lys Glu Gln
    130                 135                 140

Leu Ser Leu Lys Met Leu Ser Leu Ile Arg Ser Asn Ile Leu Lys Phe
145                 150                 155                 160

Ile Asn Lys Leu Asp Ala Leu His Val Val Asn Tyr Asn Gly Leu Leu
                165                 170                 175

Ser Ser Ile Glu Ile Gly Thr Gln Asn His Thr Ile Ile Thr Arg
            180                 185                 190

Thr Asn Met Gly Phe Leu Val Glu Leu Gln Glu Pro Asp Lys Ser Ala
        195                 200                 205
```

```
Met Asn Arg Met Lys Pro Gly Pro Ala Lys Phe Ser Leu Leu His Glu
    210                 215                 220

Ser Thr Leu Lys Ala Phe Thr Gln Gly Ser Ser Thr Arg Met Gln Ser
225                 230                 235                 240

Leu Ile Leu Glu Phe Asn Ser Ser Leu Ala Ile
                245                 250

<210> SEQ ID NO 20
<211> LENGTH: 324
<212> TYPE: PRT
<213> ORGANISM: Ebola zaire

<400> SEQUENCE: 20

Met Glu Ala Ser Tyr Glu Arg Gly Arg Pro Arg Ala Ala Arg Gln His
1               5                   10                  15

Ser Arg Asp Gly His Asp His His Val Arg Ala Arg Ser Ser Ser Arg
                20                  25                  30

Glu Asn Tyr Arg Gly Glu Tyr Arg Gln Ser Arg Ser Ala Ser Gln Val
            35                  40                  45

Arg Val Pro Thr Val Phe His Lys Lys Arg Val Glu Pro Leu Thr Val
        50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Ile Ala Arg Lys Thr Cys Gly Ser Val
                100                 105                 110

Glu Gln Gln Leu Asn Ile Thr Ala Pro Lys Asp Ser Arg Leu Ala Asn
            115                 120                 125

Pro Thr Ala Asp Asp Phe Gln Gln Glu Glu Gly Pro Lys Ile Thr Leu
        130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
    210                 215                 220

Ala Leu Trp Gln Gln Trp Asp Leu Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Ser
        275                 280                 285

Ile Gln Gln Gln Leu Ala Ser Cys Leu His Arg Thr Arg Gly Asp Trp
    290                 295                 300

His Ala Ala Leu Lys Phe Leu Tyr Phe Ser Phe Leu Phe Arg Ile
305                 310                 315                 320

Gly Phe Cys Phe
```

<210> SEQ ID NO 21
<211> LENGTH: 340
<212> TYPE: PRT
<213> ORGANISM: Ebola zaire

<400> SEQUENCE: 21

Met Thr Thr Arg Thr Lys Gly Arg Gly His Thr Ala Ala Thr Thr Gln
1               5                   10                  15

Asn Asp Arg Met Pro Gly Pro Glu Leu Ser Gly Trp Ile Ser Glu Gln
            20                  25                  30

Leu Met Thr Gly Arg Ile Pro Val Ser Asp Ile Phe Cys Asp Ile Glu
        35                  40                  45

Asn Asn Pro Gly Leu Cys Tyr Ala Ser Gln Met Gln Gln Thr Lys Pro
    50                  55                  60

Asn Pro Lys Thr Arg Asn Ser Gln Thr Gln Thr Asp Pro Ile Cys Asn
65                  70                  75                  80

His Ser Phe Glu Glu Val Val Gln Thr Leu Ala Ser Leu Ala Thr Val
                85                  90                  95

Val Gln Gln Gln Thr Ile Ala Ser Glu Ser Leu Glu Gln Arg Ile Thr
            100                 105                 110

Ser Leu Glu Asn Gly Leu Lys Pro Val Tyr Asp Met Ala Lys Thr Ile
        115                 120                 125

Ser Ser Leu Asn Arg Val Cys Ala Glu Met Val Ala Lys Tyr Asp Leu
    130                 135                 140

Leu Val Met Thr Thr Gly Arg Ala Thr Ala Thr Ala Ala Ala Thr Glu
145                 150                 155                 160

Ala Tyr Trp Ala Glu His Gly Gln Pro Pro Pro Gly Pro Ser Leu Tyr
                165                 170                 175

Glu Glu Ser Ala Ile Arg Gly Lys Ile Glu Ser Arg Asp Glu Thr Val
            180                 185                 190

Pro Gln Ser Val Arg Glu Ala Phe Asn Asn Leu Asn Ser Thr Thr Ser
        195                 200                 205

Leu Thr Glu Glu Asn Phe Gly Lys Pro Asp Ile Ser Ala Lys Asp Leu
    210                 215                 220

Arg Asn Ile Met Tyr Asp His Leu Pro Gly Phe Gly Thr Ala Phe His
225                 230                 235                 240

Gln Leu Val Gln Val Ile Cys Lys Leu Gly Lys Asp Ser Asn Ser Leu
                245                 250                 255

Asp Ile Ile His Ala Glu Phe Gln Ala Ser Leu Ala Glu Gly Asp Ser
            260                 265                 270

Pro Gln Cys Ala Leu Ile Gln Ile Thr Lys Arg Val Pro Ile Phe Gln
        275                 280                 285

Asp Ala Ala Pro Pro Val Ile His Ile Arg Ser Arg Gly Asp Ile Pro
    290                 295                 300

Arg Ala Cys Gln Lys Ser Leu Arg Pro Val Pro Pro Ser Pro Lys Ile
305                 310                 315                 320

Asp Arg Gly Trp Val Cys Val Phe Gln Leu Gln Asp Gly Lys Thr Leu
                325                 330                 335

Gly Leu Lys Ile
            340

<210> SEQ ID NO 22
<211> LENGTH: 326
<212> TYPE: PRT

<213> ORGANISM: Ebola zaire

<400> SEQUENCE: 22

Met Arg Arg Val Ile Leu Pro Thr Ala Pro Pro Glu Tyr Met Glu Ala
 1               5                  10                  15

Ile Tyr Pro Val Arg Ser Asn Ser Thr Ile Ala Arg Gly Gly Asn Ser
            20                  25                  30

Asn Thr Gly Phe Leu Thr Pro Glu Ser Val Asn Gly Asp Thr Pro Ser
        35                  40                  45

Asn Pro Leu Arg Pro Ile Ala Asp Asp Thr Ile Asp His Ala Ser His
    50                  55                  60

Thr Pro Gly Ser Val Ser Ser Ala Phe Ile Leu Glu Ala Met Val Asn
65                  70                  75                  80

Val Ile Ser Gly Pro Lys Val Leu Met Lys Gln Ile Pro Ile Trp Leu
                85                  90                  95

Pro Leu Gly Val Ala Asp Gln Lys Thr Tyr Ser Phe Asp Ser Thr Thr
            100                 105                 110

Ala Ala Ile Met Leu Ala Ser Tyr Thr Ile Thr His Phe Gly Lys Ala
        115                 120                 125

Thr Asn Pro Leu Val Arg Val Asn Arg Leu Gly Pro Gly Ile Pro Asp
    130                 135                 140

His Pro Leu Arg Leu Leu Arg Ile Gly Asn Gln Ala Phe Leu Gln Glu
145                 150                 155                 160

Phe Val Leu Pro Pro Val Gln Leu Pro Gln Tyr Phe Thr Phe Asp Leu
                165                 170                 175

Thr Ala Leu Lys Leu Ile Thr Gln Pro Leu Pro Ala Ala Thr Trp Thr
            180                 185                 190

Asp Asp Thr Pro Thr Gly Ser Asn Gly Ala Leu Arg Pro Gly Ile Ser
        195                 200                 205

Phe His Pro Lys Leu Arg Pro Ile Leu Leu Pro Asn Lys Ser Gly Lys
    210                 215                 220

Lys Gly Asn Ser Ala Asp Leu Thr Ser Pro Glu Lys Ile Gln Ala Ile
225                 230                 235                 240

Met Thr Ser Leu Gln Asp Phe Lys Ile Val Pro Ile Asp Pro Thr Lys
                245                 250                 255

Asn Ile Met Gly Ile Glu Val Pro Glu Thr Leu Val His Lys Leu Thr
            260                 265                 270

Gly Lys Lys Val Thr Ser Lys Asn Gly Gln Pro Ile Ile Pro Val Leu
        275                 280                 285

Leu Pro Lys Tyr Ile Gly Leu Asp Pro Val Ala Pro Gly Asp Leu Thr
    290                 295                 300

Met Val Ile Thr Gln Asp Cys Asp Thr Cys His Ser Pro Ala Ser Leu
305                 310                 315                 320

Pro Ala Val Ile Glu Lys
                325

<210> SEQ ID NO 23
<211> LENGTH: 288
<212> TYPE: PRT
<213> ORGANISM: Ebola zaire

<400> SEQUENCE: 23

Met Glu Ala Ser Tyr Glu Arg Gly Arg Pro Arg Ala Ala Arg Gln His
 1               5                  10                  15

Ser Arg Asp Gly His Asp His His Val Arg Ala Arg Ser Ser Ser Arg

```
                  20                  25                  30
Glu Asn Tyr Arg Gly Glu Tyr Arg Gln Ser Arg Ser Ala Ser Gln Val
        35                  40                  45

Arg Val Pro Thr Val Phe His Lys Lys Arg Val Glu Pro Leu Thr Val
    50                  55                  60

Pro Pro Ala Pro Lys Asp Ile Cys Pro Thr Leu Lys Lys Gly Phe Leu
65                  70                  75                  80

Cys Asp Ser Ser Phe Cys Lys Lys Asp His Gln Leu Glu Ser Leu Thr
                85                  90                  95

Asp Arg Glu Leu Leu Leu Leu Ile Ala Arg Lys Thr Cys Gly Ser Val
            100                 105                 110

Glu Gln Gln Leu Asn Ile Thr Ala Pro Lys Asp Ser Arg Leu Ala Asn
        115                 120                 125

Pro Thr Ala Asp Asp Phe Gln Gln Glu Glu Gly Pro Lys Ile Thr Leu
    130                 135                 140

Leu Thr Leu Ile Lys Thr Ala Glu His Trp Ala Arg Gln Asp Ile Arg
145                 150                 155                 160

Thr Ile Glu Asp Ser Lys Leu Arg Ala Leu Leu Thr Leu Cys Ala Val
                165                 170                 175

Met Thr Arg Lys Phe Ser Lys Ser Gln Leu Ser Leu Leu Cys Glu Thr
            180                 185                 190

His Leu Arg Arg Glu Gly Leu Gly Gln Asp Gln Ala Glu Pro Val Leu
        195                 200                 205

Glu Val Tyr Gln Arg Leu His Ser Asp Lys Gly Gly Ser Phe Glu Ala
    210                 215                 220

Ala Leu Trp Gln Gln Trp Asp Arg Gln Ser Leu Ile Met Phe Ile Thr
225                 230                 235                 240

Ala Phe Leu Asn Ile Ala Leu Gln Leu Pro Cys Glu Ser Ser Ala Val
                245                 250                 255

Val Val Ser Gly Leu Arg Thr Leu Val Pro Gln Ser Asp Asn Glu Glu
            260                 265                 270

Ala Ser Thr Asn Pro Gly Thr Cys Ser Trp Ser Asp Glu Gly Thr Pro
        275                 280                 285

<210> SEQ ID NO 24
<211> LENGTH: 11
<212> TYPE: PRT
<213> ORGANISM: Ebola zaire

<400> SEQUENCE: 24

Val Tyr Gln Val Asn Asn Leu Glu Glu Ile Cys
1               5                   10

<210> SEQ ID NO 25
<211> LENGTH: 23
<212> TYPE: PRT
<213> ORGANISM: Ebola zaire

<400> SEQUENCE: 25

Leu Lys Phe Ile Asn Lys Leu Asp Ala Leu Leu Val Val Asn Tyr Asn
1               5                   10                  15

Gly Leu Leu Ser Ser Ile Phe
            20

<210> SEQ ID NO 26
<211> LENGTH: 8
<212> TYPE: PRT
```

<213> ORGANISM: Ebola zaire

<400> SEQUENCE: 26

Gly Gln Phe Leu Phe Ala Ser Leu
 1               5

<210> SEQ ID NO 27
<211> LENGTH: 9
<212> TYPE: PRT
<213> ORGANISM: Ebola zaire

<400> SEQUENCE: 27

Asp Ala Val Leu Tyr Tyr His Met Met
 1               5

<210> SEQ ID NO 28
<211> LENGTH: 9
<212> TYPE: PRT
<213> ORGANISM: Ebola zaire

<400> SEQUENCE: 28

Ser Phe Lys Ala Ala Leu Ser Ser Leu
 1               5

<210> SEQ ID NO 29
<211> LENGTH: 15
<212> TYPE: PRT
<213> ORGANISM: Ebola zaire

<400> SEQUENCE: 29

Trp Ile Pro Tyr Phe Gly Pro Ala Ala Glu Gly Ile Tyr Thr Glu
 1               5                  10                  15

<210> SEQ ID NO 30
<211> LENGTH: 14
<212> TYPE: PRT
<213> ORGANISM: Ebola zaire

<400> SEQUENCE: 30

Asn Tyr Asn Gly Leu Leu Ser Ser Ile Glu Gly Thr Gln Asn
 1               5                  10

<210> SEQ ID NO 31
<211> LENGTH: 25
<212> TYPE: PRT
<213> ORGANISM: Ebola zaire

<400> SEQUENCE: 31

Arg Met Lys Pro Gly Pro Ala Lys Phe Ser Leu Leu His Glu Ser Thr
 1               5                  10                  15

Leu Lys Ala Phe Thr Gln Gly Ser Ser
            20                  25

<210> SEQ ID NO 32
<211> LENGTH: 15
<212> TYPE: PRT
<213> ORGANISM: Ebola zaire

<400> SEQUENCE: 32

Phe Ser Lys Ser Gln Leu Ser Leu Leu Cys Glu Thr His Leu Arg
 1               5                  10                  15

<210> SEQ ID NO 33
<211> LENGTH: 15

```
<212> TYPE: PRT
<213> ORGANISM: Ebola zaire

<400> SEQUENCE: 33

Asp Leu Gln Ser Leu Ile Met Phe Ile Thr Ala Phe Leu Asn Ile
1               5                   10                  15

<210> SEQ ID NO 34
<211> LENGTH: 8
<212> TYPE: PRT
<213> ORGANISM: Ebola zaire

<400> SEQUENCE: 34

Arg Asn Ile Met Tyr Asp His Leu
1               5

<210> SEQ ID NO 35
<211> LENGTH: 8
<212> TYPE: PRT
<213> ORGANISM: Ebola zaire

<400> SEQUENCE: 35

Met Val Ala Lys Tyr Asp Leu Leu
1               5

<210> SEQ ID NO 36
<211> LENGTH: 9
<212> TYPE: PRT
<213> ORGANISM: Ebola zaire

<400> SEQUENCE: 36

Cys Asp Ile Glu Asn Asn Pro Gly Leu
1               5

<210> SEQ ID NO 37
<211> LENGTH: 15
<212> TYPE: PRT
<213> ORGANISM: Ebola zaire

<400> SEQUENCE: 37

Ala Phe Leu Gln Glu Phe Val Leu Pro Pro Val Gln Leu Pro Gln
1               5                   10                  15

<210> SEQ ID NO 38
<211> LENGTH: 20
<212> TYPE: PRT
<213> ORGANISM: Ebola zaire

<400> SEQUENCE: 38

Phe Val Leu Pro Pro Val Gln Leu Pro Gln Tyr Phe Thr Phe Asp Leu
1               5                   10                  15

Thr Ala Leu Lys
            20

<210> SEQ ID NO 39
<211> LENGTH: 30
<212> TYPE: PRT
<213> ORGANISM: Ebola zaire

<400> SEQUENCE: 39

Lys Ser Gly Lys Lys Gly Asn Ser Ala Asp Leu Thr Ser Pro Glu Lys
1               5                   10                  15

Ile Gln Ala Ile Met Thr Ser Leu Gln Asp Phe Lys Ile Val
            20                  25                  30
```

-continued

<210> SEQ ID NO 40
<211> LENGTH: 15
<212> TYPE: PRT
<213> ORGANISM: Ebola zaire

<400> SEQUENCE: 40

Pro Leu Arg Leu Leu Arg Ile Gly Asn Gln Ala Phe Leu Gln Glu
 1               5                  10                  15

<210> SEQ ID NO 41
<211> LENGTH: 15
<212> TYPE: PRT
<213> ORGANISM: Ebola zaire

<400> SEQUENCE: 41

Arg Ile Gly Asn Gln Ala Phe Leu Gln Glu Phe Val Leu Pro Pro
 1               5                  10                  15

<210> SEQ ID NO 42
<211> LENGTH: 9
<212> TYPE: PRT
<213> ORGANISM: Ebola zaire

<400> SEQUENCE: 42

Tyr Phe Gly Pro Ala Ala Glu Gly Ile
 1               5

<210> SEQ ID NO 43
<211> LENGTH: 9
<212> TYPE: PRT
<213> ORGANISM: Ebola zaire

<400> SEQUENCE: 43

Lys Phe Ile Asn Lys Leu Asp Ala Leu
 1               5

<210> SEQ ID NO 44
<211> LENGTH: 9
<212> TYPE: PRT
<213> ORGANISM: Ebola zaire

<400> SEQUENCE: 44

Asn Tyr Asn Gly Leu Leu Ser Ser Ile
 1               5

<210> SEQ ID NO 45
<211> LENGTH: 9
<212> TYPE: PRT
<213> ORGANISM: Ebola zaire

<400> SEQUENCE: 45

Pro Gly Pro Ala Lys Phe Ser Leu Leu
 1               5

<210> SEQ ID NO 46
<211> LENGTH: 10
<212> TYPE: PRT
<213> ORGANISM: Ebola zaire

<400> SEQUENCE: 46

Leu Ser Leu Leu Cys Glu Thr His Leu Arg
 1               5                  10

```
<210> SEQ ID NO 47
<211> LENGTH: 9
<212> TYPE: PRT
<213> ORGANISM: Ebola zaire

<400> SEQUENCE: 47

Met Phe Ile Thr Ala Phe Leu Asn Ile
  1               5

<210> SEQ ID NO 48
<211> LENGTH: 9
<212> TYPE: PRT
<213> ORGANISM: Ebola zaire

<400> SEQUENCE: 48

Glu Phe Val Leu Pro Pro Val Gln Leu
  1               5

<210> SEQ ID NO 49
<211> LENGTH: 6
<212> TYPE: PRT
<213> ORGANISM: Ebola zaire

<400> SEQUENCE: 49

Phe Leu Val Pro Pro Val
  1               5

<210> SEQ ID NO 50
<211> LENGTH: 11
<212> TYPE: PRT
<213> ORGANISM: Ebola zaire

<400> SEQUENCE: 50

Gln Tyr Phe Thr Phe Asp Leu Thr Ala Leu Lys
  1               5                  10

<210> SEQ ID NO 51
<211> LENGTH: 9
<212> TYPE: PRT
<213> ORGANISM: Ebola zaire

<400> SEQUENCE: 51

Thr Ser Pro Glu Lys Ile Gln Ala Ile
  1               5

<210> SEQ ID NO 52
<211> LENGTH: 8
<212> TYPE: PRT
<213> ORGANISM: Ebola zaire

<400> SEQUENCE: 52

Arg Ile Gly Asn Gln Ala Phe Leu
  1               5

<210> SEQ ID NO 53
<211> LENGTH: 8
<212> TYPE: PRT
<213> ORGANISM: Ebola zaire

<400> SEQUENCE: 53

Gln Ala Phe Leu Gln Glu Phe Val
  1               5
```